US012668567B2

(12) United States Patent
Anderson et al.

(10) Patent No.: US 12,668,567 B2
(45) Date of Patent: Jun. 30, 2026

(54) MODIFIED FORMS OF AMBROXOL FOR THERAPEUTIC USE

(71) Applicant: Zywie, LLC, Princeton, NJ (US)

(72) Inventors: Stephen Anderson, Princeton, NJ (US); Stephen Pasternak, London (CA); Vincent Jacques, Somerville, MA (US); Gerard Joseph Broussard, Jr., Langhorne, PA (US)

(73) Assignee: Zywie, LLC, Princeton, NJ (US)

( * ) Notice: Subject to any disclaimer, the term of this patent is extended or adjusted under 35 U.S.C. 154(b) by 0 days.

(21) Appl. No.: 18/780,126

(22) Filed: Jul. 22, 2024

(65) Prior Publication Data

US 2025/0011277 A1 Jan. 9, 2025

Related U.S. Application Data

(63) Continuation of application No. PCT/US2024/027209, filed on May 1, 2024.

(60) Provisional application No. 63/499,613, filed on May 2, 2023.

(51) Int. Cl.

| | |
|---|---|
| ***C07C 215/44*** | (2006.01) |
| ***A61K 9/48*** | (2006.01) |
| ***A61K 9/50*** | (2006.01) |
| ***A61K 31/137*** | (2006.01) |
| ***A61P 25/16*** | (2006.01) |
| ***A61P 25/28*** | (2006.01) |
| ***A61P 43/00*** | (2006.01) |
| ***C07C 217/84*** | (2006.01) |

(52) U.S. Cl.

CPC .......... *C07C 215/44* (2013.01); *A61K 9/4866* (2013.01); *A61K 9/5015* (2013.01); *A61K 9/5047* (2013.01); *A61K 31/137* (2013.01); *A61P 25/16* (2018.01); *A61P 25/28* (2018.01); *A61P 43/00* (2018.01); *C07C 217/84* (2013.01)

(58) Field of Classification Search

CPC ...... C07C 215/42; C07C 215/44; A61P 11/00; A61P 11/16

See application file for complete search history.

(56) References Cited

U.S. PATENT DOCUMENTS

| | | | |
|---|---|---|---|
| 3,448,106 | A | 6/1969 | Josef et al. |
| 5,654,303 | A | 8/1997 | Kornberg et al. |
| 2015/0258081 | A1 | 9/2015 | Lukas et al. |

FOREIGN PATENT DOCUMENTS

| | | | | | |
|---|---|---|---|---|---|
| CN | 115518058 | A | * | 12/2022 | .............. A61P 31/12 |
| JP | H045265 | A | | 1/1992 | |
| JP | H11124369 | A | | 5/1999 | |
| WO | WO-2016154313 | A1 | * | 9/2016 | ........... A61K 31/137 |
| WO | WO-2019018247 | A1 | * | 1/2019 | ................ A61P 9/10 |
| WO | WO-2019147931 | A1 | * | 8/2019 | ........... A61K 31/137 |
| WO | WO-2019243530 | A1 | * | 12/2019 | ........... C07D 405/14 |

OTHER PUBLICATIONS

Liu et al (APOE genetype and neuroimaging markers of Alzheimeras disease: systemic review and meta-analysis, J Neurol Neurosurg Psychiatry, 2015; 86(2); 127-134 (Year: 2015).*

Thijssen et al (Plasma phosphorylated tau 217 and phosphorylated tau 181 as biomarkers in Alzheimerâs disease and frontotemperoal lobar degeneration: a retrospective diagnostic performance study, Lancet Neurol; 20: 739-52 (Year: 2021).*

Liu et al (APOE gene type and neuroimaging markers of Alzheimer's Disease: systemic review and meta-analysis, J Neurol Neurosurg Psychiatry, 2015; 86 (2); 127-134 (Year: 2015).*

Thijssen et al (Plasma phosphorylated tau 217 and phosphorylate tau 181 as biomarkers in Alzheimer's Disease and frontotemperoal lobar degeneration: a retrospective diagnostic performance study, Lancet Neurol; 20: 739-52 (Year: 2021).*

International Search Report received in corresponding PCT Application PCT/US24/27209.

Written Opinion received in corresponding PCT Application PCT/US24/27209.

International Preliminary Report on Patentability received in corresponding PCT application PCT/US24/27209.

* cited by examiner

*Primary Examiner* — Micah Paul Young

(74) *Attorney, Agent, or Firm* — Michele M. Wales; InHouse Patent Counsel

(57) ABSTRACT

The invention relates to analog forms of ambroxol and related compounds, compositions comprising same, and methods of preventing and/or treating various diseases and medical conditions involving the administration of analogs of ambroxol and related compounds.

26 Claims, 11 Drawing Sheets

FIG. 1
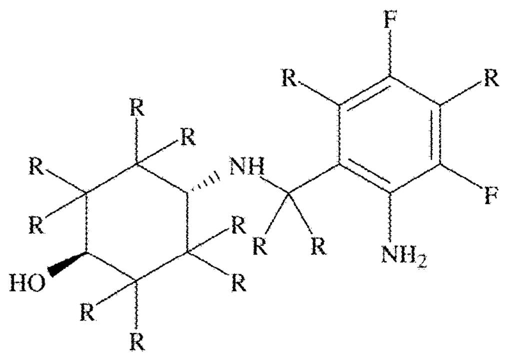
1
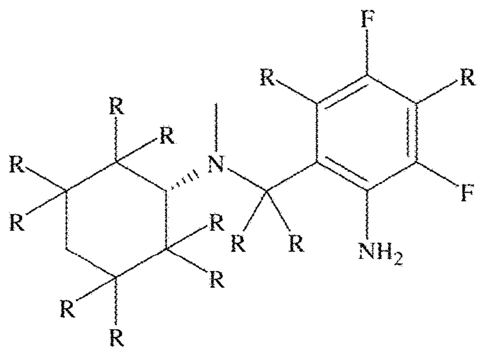
2
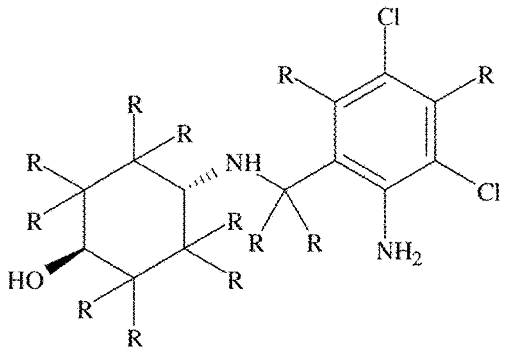
3
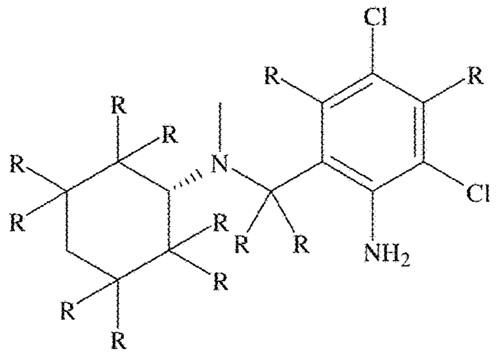
4
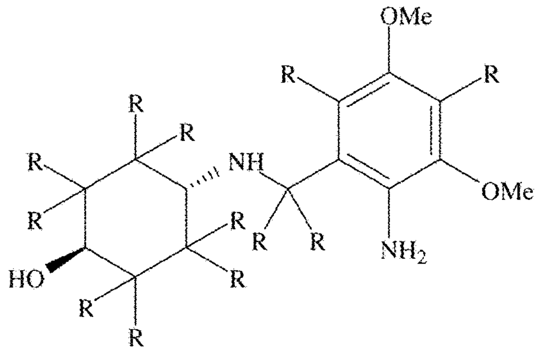
5
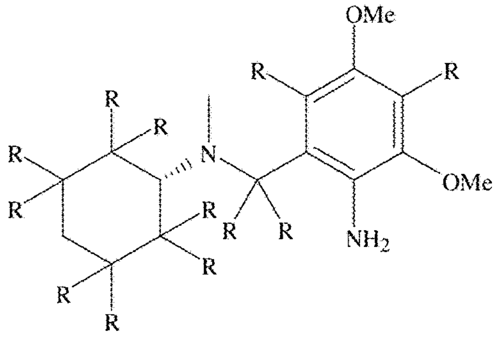
6

FIG. 10A-D
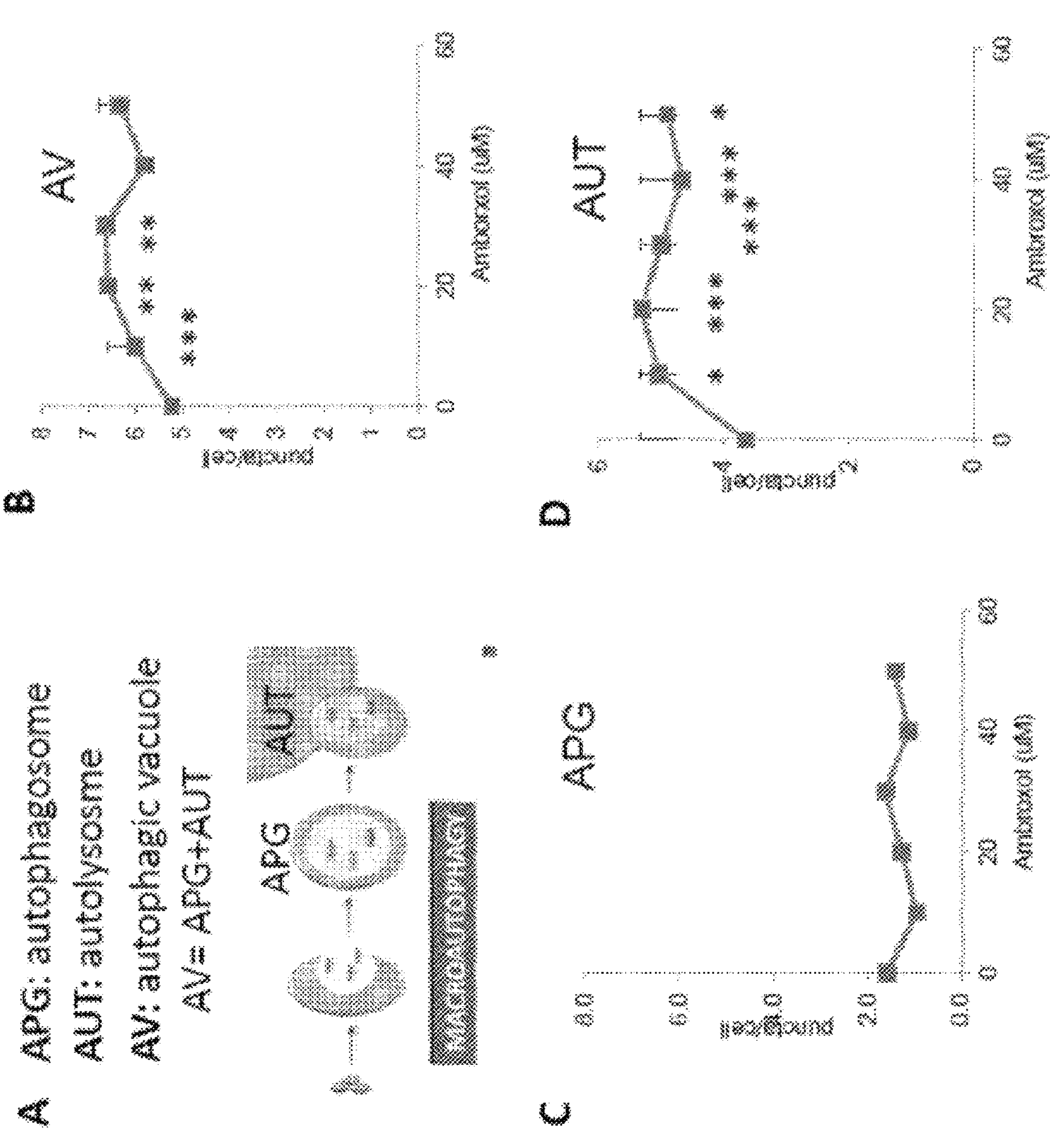

FIG. 11A-B
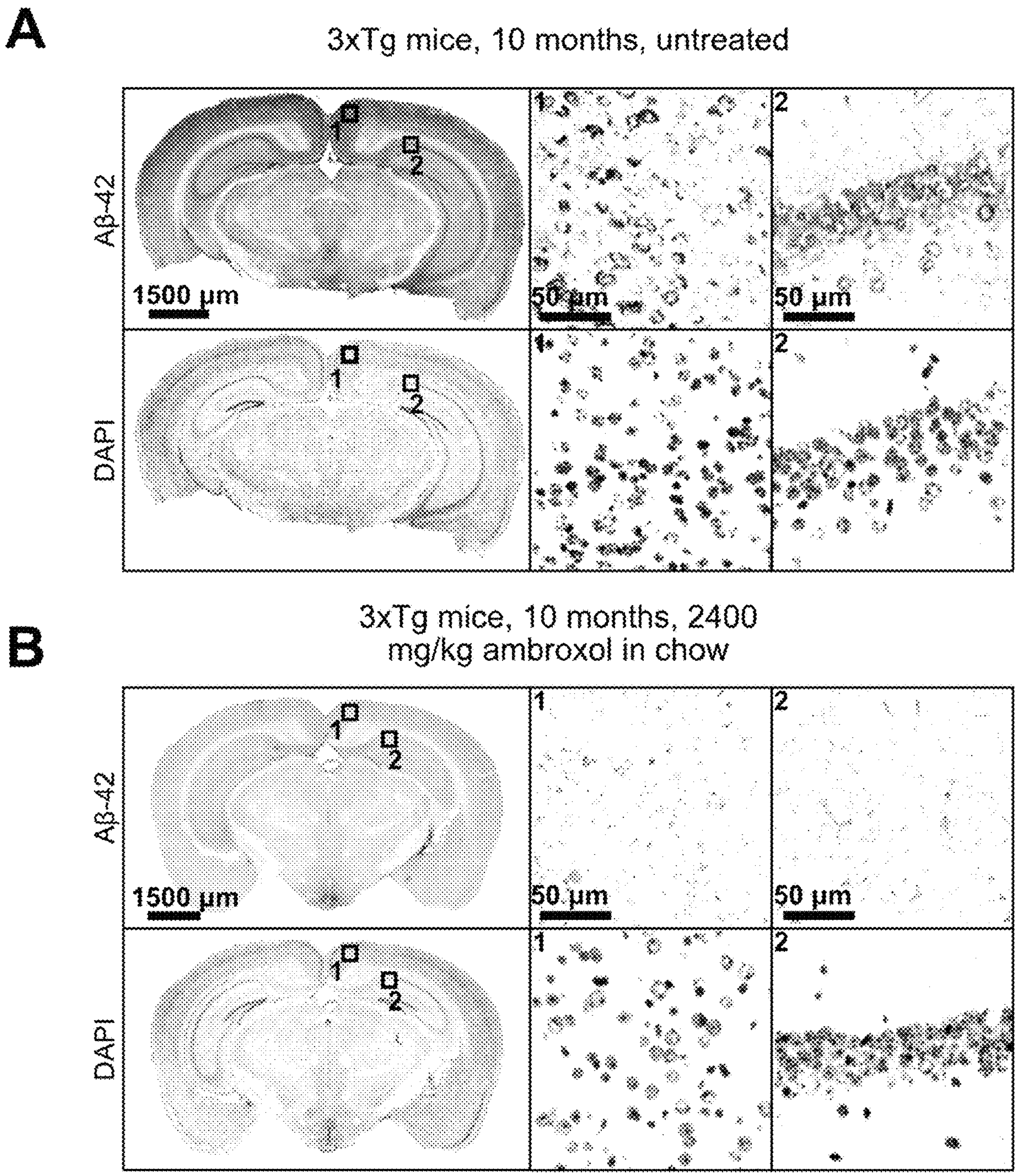

MODIFIED FORMS OF AMBROXOL FOR THERAPEUTIC USE

CROSS-REFERENCE TO RELATED APPLICATIONS

This application is a Continuation of and claims priority to PCT/US24/27209 filed on May 1, 2024, which claims priority to U.S. 63/499,613 filed on May 2, 2023, both of which are hereby incorporated by reference in their entirety.

BACKGROUND OF THE INVENTION

Field of the Invention

The invention relates to derivatives or analogues of ambroxol, ambroxol hydrochloride, and/or bromhexine suitable for use in various therapeutic applications.

DISCUSSION OF THE RELATED ART

Ambroxol, ambroxol hydrochloride and the structurally-related "parent compound" bromhexine, are mucolytic agents that have been available in a number of countries since the late 1970s for use in the treatment of acute and chronic respiratory diseases and conditions associated with the production of excess and/or highly viscous mucus.

By triggering lysosomal exocytosis via pH-dependent calcium release from acidic calcium stores (Fois G et al., *Cell Calcium* 58(6):628-637, 2015), it is thought that ambroxol acts to promote mucus clearance by, for example, breaking up phlegm, and stimulating the production of surfactant by type II pneumocytes (Seiffert C et al., *Toxicol Appl Pharmacol* 203(1):27-35, 2005) to reduce adhesion of mucus to the walls of the respiratory tract. In addition, it has been found that ambroxol potently inhibits neuronal sodium channels to enable, especially when administered in the form of a lozenge, rapid pain relief used in acute sore throat (de Mey C et al., *Arzneimittel-Forschung* 28(5a):889-898, 1978).

In more recent times, there has been wide interest in the repurposing of ambroxol for a number of other medical uses. For example, it has been reported that ambroxol can act as a "molecular chaperone" for the lysosomal enzyme beta-glucocerebrosidase (GCase, UniProtKB Entry P04062) to thereby increase the amounts and activity of this enzyme. This may mean that ambroxol might be suitable for the treatment of Gaucher's disease (Maegawa G H B et al., *J Biol Chem* 284(35):23502-23516, 2009) which is the most prevalent lysosomal storage disease and is caused by a deficiency in GCase. Similarly, this ability to increase the activity of GCase may be beneficial for the treatment of Parkinson's disease (PD) in individuals with loss-of-function mutations in the glucocerebrosidase gene, GBA1, (McNeill A et al., *Brain* 137(5):1481-1495, 2014). In a recent report, it has been shown that daily ambroxol administration was able to increase brain GCase activity in healthy, non-human primates. Migdalska-Richards A et al., *Synapse* 71(7):e21967, 2017. Ambroxol has also been shown to increase transcription factor EB (TFEB), a master regulator of autophagosomal/lysosomal genes, leading to increase in other lysosomal proteins including the protease Cathepsin D. See, e.g., Magalhaes, J., Gegg, M. E., Migdalska-Richards, A., Schapira, A. H., 2018. Effects of ambroxol on the autophagy-lysosome pathway and mitochondria in primary cortical neurons. Sci Rep-uk 8, 1385.

Accordingly, ambroxol continues to be the subject of considerable research interest and effort. The present inventors, in the course of their work towards identifying and developing new therapeutic methods and compositions based upon ambroxol, have designed novel modified forms of ambroxol (i.e., ambroxol analogs). It is considered that these modified compounds may offer one or more advantage over one or more of ambroxol, ambroxol hydrochloride and bromhexine such as, for example, greater stability leading to an increased half-life and duration of action in the body.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The invention relates to analog forms of ambroxol and related compounds, compositions comprising same, and methods of preventing and/or treating various diseases and medical conditions involving the administration of analogs of ambroxol and related compounds.

More specifically, the invention provides a compound according to Formula I:

I

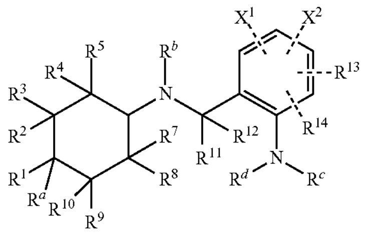

wherein

...... indicates that the associated R or X group can be attached to any available carbon atom on the phenyl ring, $R^a$ is selected from H, hydroxyl (OH), lower alkyl (e.g., $C_{1-3}$ alkyl such as $CH_3$ and $CH_2CH_3$), and lower alcohol (e.g., $C_{1-3}$ alcohol such as $CH_2OH$), $R^b$ is selected from H and lower alkyl (e.g., $C_{1-3}$ alkyl such as $CH_3$ and $CH_2CH_3$), $R^c$ and $R^d$ are each independently selected from H, lower alkyl (e.g., $C_{1-3}$ alkyl such as $CH_3$ and $CH_2CH_3$) or $R^c$ and $R^d$ are each part of a 4, 5, 6 or 7 membered ring structure that connects $R^c$ and $R^d$ (e.g., —$R^c$—N—$R^d$—$(CH2)_n$— where n is an integer selected from 1, 2, 3 and 4), each of $R^1$ to $R^{14}$ is independently selected from H and D, $X^1$ and $X^2$ are independently selected from F, Cl, Br, I, lower alkyl (e.g., $C_{1-3}$ alkyl such as $CH_3$ and $CH_2CH_3$), lower alkoxy (e.g., $C_{1-3}$ alkoxy such as $OCH_3$ and $OCH_2CH_3$), lower alkylamine (e.g., $C_{1-3}$ alkylamine such as $NR^bCH_3$ and $NR^bCH_2CH_3$), lower acyl (e.g., $C_{2-4}$ acyl such as $C(O)CH_3$ and $C(O)CH_2CH_3$), nitro ($NO_2$), nitrile (CN), sulfoxide (SO—R), sulfonate (SO2-R), and sulfate (O-SO2-O—R), with the proviso that $X^1$ and $X^2$ are not both Br; or a pharmaceutically acceptable salt, solvate or prodrug thereof.

In certain embodiments, the invention provides a compound according to Formula Ia:

I

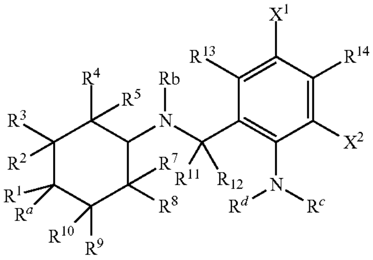

wherein $R^a$, $R^b$, $R^c$, $R^d$, $R^1$ to $R^{14}$, $X^1$ and $X^2$ are as described for the compounds of Formula I, with the proviso that $X^1$ and $X^2$ are not both Br; or a pharmaceutically acceptable salt, solvate or prodrug thereof.

Optionally, it is contemplated that any or all H atoms in the compound of Formula I may be replaced by a deuterium atom.

The analogs as shown herein have unexpectedly demonstrated improved metabolic stability, which leads to an improvement in the overall cost of goods of the analogs. Additionally, increased stability of the analogs may also allow for a higher exposure of the analog when administered. Moreover, the improved stability of the analog may also allow for a reduced dosing schedule as compared to ambroxol alone. An additional potential benefit of the compounds according to Formula I is resistance to metabolism (as compared to the ambroxol) such as, for example, metabolism through cleavage (e.g., via oxidation) of the covalent carbon-nitrogen bond of the linking group between the ring structures of compounds according to Formula I.

The invention also provides a pharmaceutical composition comprising a compound of Formula I (or a pharmaceutically acceptable salt, solvate or prodrug thereof), and methods of preventing and/or treating various diseases and medical conditions in a subject involving the administration of a compound of Formula I (or a pharmaceutically acceptable salt, solvate or prodrug thereof).

More specifically, the invention provides methods of preventing and/or treating a disease or medical condition selected from the group consisting of respiratory diseases and conditions (e.g., bronchopulmonary diseases, and especially those associated with the production of excess and/or highly viscous mucus) and including pain associated with acute sore throat, lysosomal storage disorders (LSDs) such as Gaucher's disease, neurological diseases and conditions (e.g., PD and other aging-associated diseases involving dysfunction of autophagy (Dockrill P., *Science Alert*, February, 2020).

Additionally, the invention provides methods of treating, reducing and/or stabilizing the symptoms associated with neurological diseases and conditions such as Alzheimer's disease (AD), Parkinson's disease (PD) Huntington's Disease, Frontotemporal Dementia, Pick's Disease, Gaucher's Disease and Amyotrophic Lateral Sclerosis (i.e., Lou Gehrig's Disease).

Further, the invention provides methods of extending life expectancy of a subject. Specifically, compounds of Formula I may be used in a method of (a) treating, inhibiting, or reducing aging of a subject, (b) treating, inhibiting, or reducing an age-related symptom or an age-related disease in a subject, and/or (c) increasing the healthspan, lifespan, and/or mental acuity of a subject.

In preferred embodiments, the subject is a mammal, and in even further preferred embodiments, the mammal is a human, a domesticated animal (e.g., a dog, a cat, a horse) or a farm animal (e.g., a cow or a pig).

BRIEF DESCRIPTION OF THE FIGURES

The objects and features of the invention can be better understood with reference to the following detailed description and accompanying drawings.

FIG. 1 provides the structures of representative compounds (compounds 1 to 6) of the invention.

FIG. 10A-D shows the effect of ambroxol on basal macroautophagy in mouse cells. Mouse fibroblasts in culture (NIH3T3 cells) expressing the tandem reporter mCherry-GFP-LC3 were exposed to the indicated concentrations of ambroxol for 24 h in complete media. FIG. 10A. Schematic of the autophagic compartments analyzed. FIG. 10B-D. Number of autophagic vacuoles (AV) (FIG. 10B); autophagosomes (APG) (FIG. 10C); and autolysosomes (AUT) (FIG. 10D). All values are mean+s.e.m. and quantifications were done in at least 2,500 cells per condition in three different experiments using high content microscopy. Differences with untreated (0 μM ambroxol) are significant for *$p<0.05$ $p<0.01$ and *$p<0.001$.

FIG. 11A-B shows the results of ambroxol treatment in an AD mouse model.

DETAILED DESCRIPTION

I. Definitions

Figure 2:
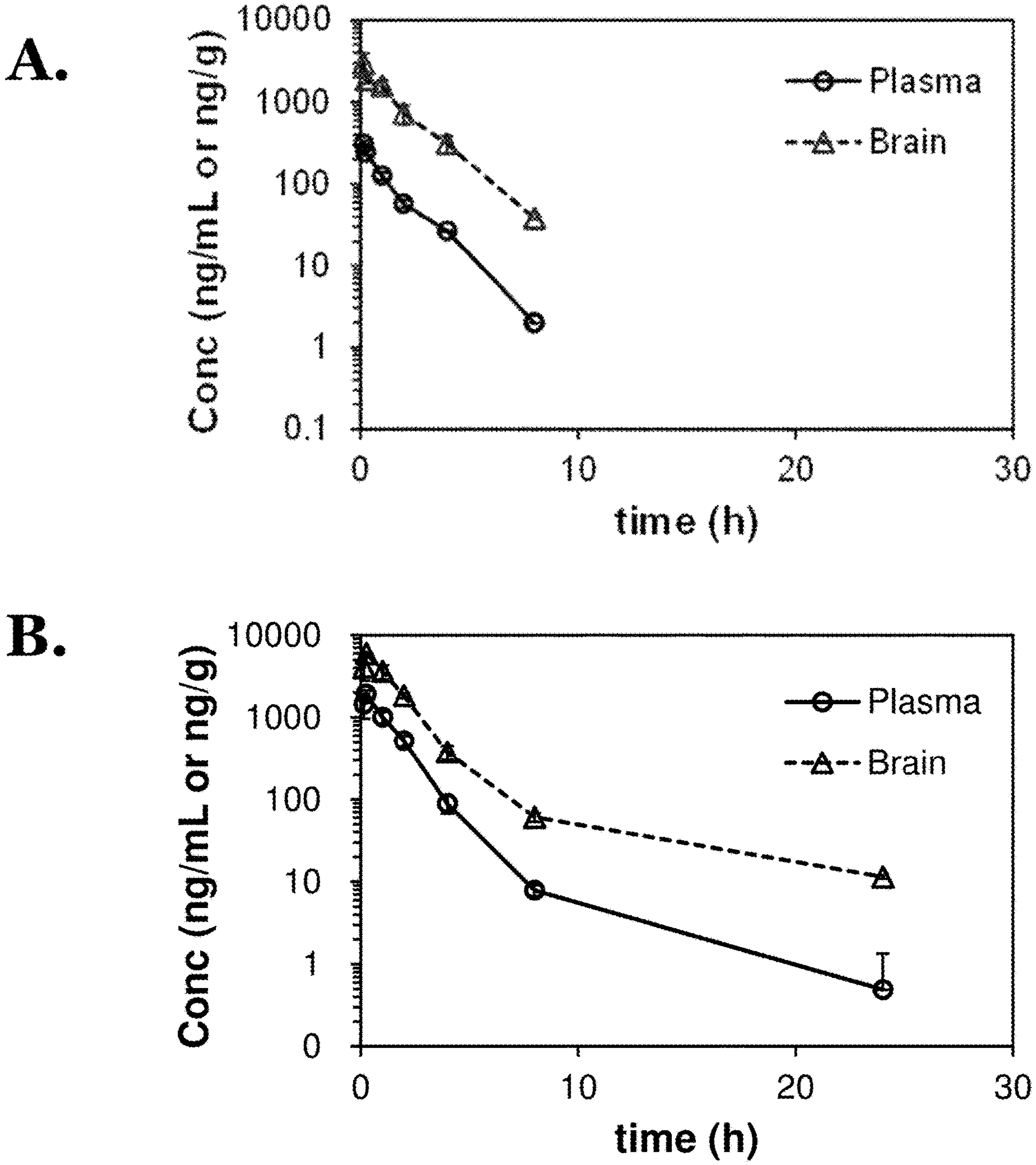
FIG. 2A-B shows average (± standard deviation) plasma and brain concentration (ng/mL and ng/g, respectively) vs. time (h) profiles in female C57BL/6 mice orally administered a single dose of ambroxol hydrochloride (FIG. 2A) versus ZW-010 HCl (Compound 1; also referred to herein as "ZW-010;" 10 mg/kg, free base equivalent) (FIG. 2B). These results demonstrate that the halogen analogs of ambroxol have substantially improved exposure in brain tissue, making these compounds ideal for treatment of the neurological disorders described herein.

The following definitions are provided for specific terms which are used in the following written description.

As used in the specification and claims, the singular form "a", "an" and "the", include plural references unless the context dearly dictates otherwise.

The present invention can "comprise" (open ended) or "consist essentially of" the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention.

As used herein, a "subject" is a vertebrate, preferably a mammal, more preferably a human, and even more preferably a domesticated animal, such as a pet, or a farm animal. Mammals include, but are not limited to, murines, simians, humans, farm animals, sport animals, and pets. In other preferred embodiments, the "subject" is a rodent (e.g., a guinea pig, a hamster, a rat, a mouse), murine (e.g., a mouse), canine (e.g., a dog), feline (e.g., a cat), equine (e.g., a horse), a primate, simian (e.g., a monkey or ape), a monkey (e.g., marmoset, baboon), or an ape (e.g., gorilla, chimpanzee, orangutan, gibbon). In other embodiments, non-human mammals, especially mammals that are conventionally used as models for demonstrating therapeutic efficacy in humans (e.g., murine, primate, porcine, canine, or rabbit animals) may be employed. In preferred embodiments, an "individual" or "patient" (as in the subject of the treatment) means mammals, particularly non-human primates, e.g., apes and monkeys, and most particularly humans.

As understood herein, an "effective amount" of a pharmaceutical composition of the present invention refers to an amount of the composition suitable to elicit a therapeutically beneficial response in the subject, e.g., promoting mucus clearance associated with respiratory diseases and conditions, providing relief from pain associated with acute sore throat, amelioration of symptoms associated with lysosomal storage disorders (LSDs) and neurological diseases and conditions, or extending and/or increasing and/or improving healthspan, lifespan and/or mental acuity, such as for example, increasing survival and/or healthy aging and/or decreasing morbidity or age-related illness in the subject.

The term "dose" or "dosage" as used herein refers to physically discrete units suitable for administration to a subject, each dosage containing a predetermined quantity of the active pharmaceutical ingredient calculated to produce a desired response.

The term "about" or "approximately" means within an acceptable range for the particular value as determined by those skilled in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Unless otherwise stated, the term "about' means within an acceptable error range for the particular value, such as ±1-20%, preferably 1-10% and more preferably ±1-5%. In even further embodiments, "about" should be understood to mean+/−5%.

Where a range of values is provided, it is understood that each intervening value, between the upper and lower limits of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All percentages and ratios used herein are by weight of the total composition unless otherwise indicated herein. All temperatures are in degrees Celsius unless specified otherwise. All measurements made are at 25° C. and normal pressure unless otherwise designated.

All ranges recited herein include the endpoints, including those that recite a range "between" two values. Terms such as "about," "generally," "substantially," "approximately" and the like are to be construed as modifying a term or value such that it is not an absolute, but does not read on the prior art. Such terms will be defined by the circumstances and the terms that they modify as those terms are understood by those skilled in the art. This includes, at the very least, the degree of expected experimental error, technique error and instrument error for a given technique used to measure a value.

Where used herein, the term "and/or" when used in a list of two or more items means that any one of the listed characteristics can be present, or any combination of two or more of the listed characteristics can be present. For example, if a composition of the present invention is described as containing characteristics A, B, and/or C, the composition can contain A feature alone; B alone; C alone; A and B in combination; A and C in combination; B and C in combination; or A, B, and C in combination.

As used herein, the term "lower alkyl" includes straight chain alkyl groups, branched alkyl groups and cyclic alkyl groups having from 1 to 8 carbon atoms (e.g., methyl, ethyl, propyl, isopropyl, butyl, isobutyl, tert-butyl, pentyl, hexyl, cyclopropyl, cyclobutyl, cyclopentyl, etc.).

As used herein, the term "lower alcohol" includes alcohol groups comprising straight chain, branched or cyclic alkyl groups having from 1 to 8 carbon atoms and 1 or more hydroxyl (OH) groups (e.g., methanol, ethanol, propanol, etc.).

The term "pharmaceutically acceptable salt" as used herein, refers to salts that retain the desired biological activity of the compound of Formula I, and include pharmaceutically acceptable acid addition salts and base addition salts. Suitable pharmaceutically acceptable acid addition salts of the compounds of Formula I may be prepared from an inorganic acid or from an organic acid. Examples of such inorganic acids are hydrochloric, sulfuric and phosphoric acid. Appropriate organic acids may be selected from aliphatic, cycloaliphatic, aromatic, heterocyclic, carboxylic and sulfonic classes of organic acids, examples of which are formic, acetic, propionic, succinic, glycolic, gluconic, lactic, malic, tartaric, citric, fumaric, maleic, alkylsulfonic and arylsulfonic. Additional information on pharmaceutically acceptable salts can be found in Remington's Pharmaceutical Sciences, 19th Edition, Mack Publishing Co, Easton PA 1995.

The term "solvate" refers to any form of a compound of Formula I, resulting from solvation of with an appropriate solvent. Such a form may be, for example, a crystalline solvate or a complex that may be formed between the solvent and the dissolved compound.

The term "prodrug" means a compound that undergoes conversion to a compound of Formula I within a biological system, usually by metabolic means (e.g., by hydrolysis, reduction or oxidation). For example, an ester prodrug of a compound of Formula I containing a hydroxyl group may be convertible by hydrolysis in vivo to the compound of Formula I. Suitable esters of the compounds of Formula I containing a hydroxyl group may be, for example, acetates, citrates, lactates, tartrates, malonates, oxalates, salicylates, propionates, succinates, fumarates, maleates, methylene-bis-P-hydroxynaphthoates, gestisates, isethionates, di-p-toluoyltartrates, methanesulfonates, ethanesulfonates, benzenesulfonates, p-toluenesulfonates, cyclohexylsulfamates and quinates. As another example, an ester prodrug of a compound of Formula I containing a carboxy group may be convertible by hydrolysis in vivo to the compound of Formula I. Examples of ester prodrugs include those described by Leinweber F J, Drug Metab Rev 18:379-439 (1987). Similarly, an acyl prodrug of a compound of Formula I containing an amino group may be convertible by hydrolysis in vivo to the compound of Formula I. Examples of prodrugs for these and other functional groups, including amines, are provided in Prodrugs: challenges and rewards, Valentino J Stella (ed), Springer, 2007.

A "derivative" compound, as the term is used herein, refers to a second compound that is derived from a first compound, such as a brominated version of a non-brominated parent compound. For example, ambroxol is a derivative of the parent compound, bromhexine.

As used herein, "lifespan" means the time until death. As used herein "healthspan" or "healthy aging" means the time of life living free (or optimally free) of serious disease. As used herein, "mental acuity" is a measure of a subject's cognitive abilities, such as ability to focus, attention span, and sharpness.

As used herein, "nutrient sensing" is a cell's ability to sense and respond to fluctuations in nutrient levels as is described in Efeyan et al., "Nutrient Sensing Mechanisms and Pathways," Nature 517: 302-310 (2015) (hereby incorporated by reference in its entirety).

As used herein "treating, inhibiting, and/or reducing aging, an age-related symptom, and/or an age-related disease" or the like means reducing the risk of occurrence, delaying the onset, slowing the progression, and/or reducing the severity and/or manifestation, of a sign of aging and/or degenerative disorder, and includes, but is not limited to, preventing the occurrence, development or progression of a sign of aging and/or degenerative disorder.

The term "pharmaceutically acceptable carrier" as used herein means any carrier, diluent or excipient which is compatible with the other ingredients of a composition and which is not deleterious to the intended subject receiving the composition.

Compounds of the Invention

The compounds of the invention are analog forms of ambroxol and related compounds (including bromhexine and ambroxol hydrochloride) as defined by Formula I. Table 1 shows the structures of ambroxol (also known by its chemical name trans-4-((2-amino-3,5-dibromobenzyl) amino) cyclohexanol), bromhexine (also known by its chemical name 2-amino-3,5-dibromo-N-cyclohexyl-N-methylbenzenemethanamine) and ambroxol hydrochloride.

TABLE 1

| Structures of ambroxol, bromhexine and ambroxol hydrochloride | |
|---|---|
| Ambroxol | 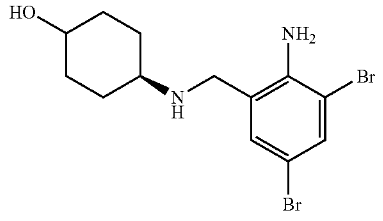 ambroxol |
| Bromhexine | 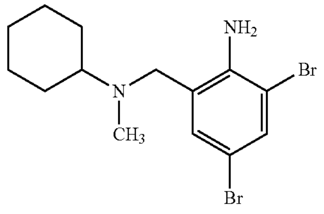 bromhexine |

TABLE 1-continued

Structures of ambroxol, bromhexine and ambroxol hydrochloride

Ambroxol Hydrochloride

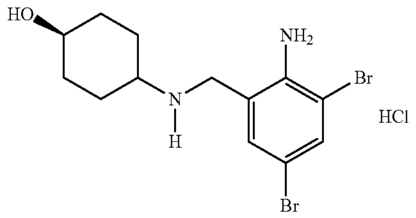

In some embodiments, the compound is selected from the halogen or alkoxy analogs of ambroxol and bromhexine shown in FIG. 1. It is considered that these compounds may show resistance to metabolism (as compared to the corresponding ambroxol or bromhexine compound) such as, for example, metabolism through cleavage (e.g., via oxidation) of the covalent carbon-nitrogen bond of the linking group between the ring structures of compounds according to Formula I, or oxidation of a carbon-hydrogen bond of the aromatic ring to form a phenolic metabolite. In other words, these compounds may have greater stability.

The compounds of the invention may be used in methods of preventing and/or treating various diseases and medical conditions including respiratory diseases and conditions, lysosomal storage disorders (LSDs), and neurological diseases and conditions, and may also be used in methods of extending life expectancy of a subject. In such methods, compounds of the invention showing greater stability (e.g., as compared to a corresponding compound lacking deuteration), may exhibit, for example, one or more advantageous pharmacokinetic properties.

Preparation of Compounds of the Invention

The compounds of the invention may be prepared by methods known to those skilled in the art of organic synthesis. For example, U.S. Patent Application publication number US 2004/0242700, incorporated herein by reference in its entirety, provides a synthetic protocol for the preparation of ambroxol. This protocol may be readily adapted to enable the synthesis of analog forms of ambroxol and related compounds. In addition, a protocol for the synthesis of ambroxol and related compounds including deuterium-containing analogs, is disclosed in Latli B et al., J Label Compd Radiopharm 53:15-23, 2010 (incorporated herein by reference in its entirety), which may also be readily adapted for the preparation of a compound of Formula I. For example, "Scheme 4" of Latli et al., 2010 may be adapted for the preparation of a compound of Formula I by substituting the 2-amino-3,5-dibromobenzaldehyde with the corresponding analog of that compound. Furthermore, compounds of the invention may be prepared by methods such as those exemplified herein.

Salts of Compounds of the Invention

For compounds that typically contain acidic or basic groups (such as carboxyl or amino groups) such groups will not necessarily be in the free acid or free base form. When referring to compounds of the invention, the reference is intended to include salt forms of the compound. Within the scope of the invention, therefore, are salts of compounds of Formula I. The preferred salts are pharmaceutically acceptable salts.

The term "salts" embraces addition salts of free acids or free bases. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification, or formulation of therapeutic compounds.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, p-hydroxybutyric, salicylic, galactaric, oxalic, malonic and galacturonic acid. Examples of pharmaceutically unacceptable acid addition salts include, for example, perchlorates and tetrafluoroborates. All these acid addition salts may be prepared from compounds of Formula I by reacting, for example, the appropriate acid with the particular compound.

Suitable pharmaceutically acceptable base addition salts of compounds of Formula I include, for example, metallic salts including alkali metal, alkaline earth metal and transition metal salts such as, for example, calcium, magnesium, potassium, sodium, and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methyl glucamine) and procaine. Examples of pharmaceutically unacceptable base addition salts include lithium salts and cyanate salts. All these base addition salts may be prepared from compounds of Formula I by reacting, for example, the appropriate base with the particular compound.

Methods Using Compounds of the Invention

As mentioned above, the compounds of the invention may be used in methods of preventing and/or treating various diseases and medical conditions including respiratory diseases and conditions, lysosomal storage disorders (LSDs), and neurological diseases and conditions, and may also be used in methods of extending life expectancy of a subject. For example, compounds of Formula I may be used in a method of (a) treating, inhibiting, or reducing aging of a subject, (b) treating, inhibiting, or reducing an age-related symptom or an age-related disease in a subject, and/or (c) increasing the healthspan, lifespan, and/or mental acuity of a subject.

In some other embodiments, the invention relates, more specifically, to a method of preventing and/or treating a disease or medical condition in a subject, wherein the disease or condition is selected from the group consisting of respiratory diseases and conditions (e.g., bronchopulmonary diseases, and especially those associated with the production of excess and/or highly viscous mucus) and including pain associated with acute sore throat, lysosomal storage disorders (LSDs) such as Gaucher's disease, and neurological diseases and conditions (e.g., Parkinson's Disease (PD), Alzheimer's disease (AD), Huntington's Disease, Frontotemporal Dementia, Pick's Disease, Gaucher's Disease and Amyotrophic Lateral Sclerosis (i.e., Lou Gehrig's Disease)

and other aging-associated diseases involving dysfunction of autophagy), wherein said method comprises administering to the subject an effective amount of a compound of Formula I (or a pharmaceutically acceptable salt, solvate or prodrug thereof). The invention also relates to the use of a compound of Formula I (or a pharmaceutically acceptable salt, solvate or prodrug thereof) as a medicament for preventing and/or treating a disease or medical condition selected from respiratory diseases and conditions, lysosomal storage disorders (LSDs) and neurological diseases and conditions. In addition, the invention relates to a pharmaceutical composition for a treatment of a disease or medical condition selected from respiratory diseases and conditions, lysosomal storage disorders (LSDs) and neurological diseases and conditions, comprising a therapeutically effective amount of a compound of Formula I (or a pharmaceutically acceptable salt, solvate or prodrug thereof), together with a pharmaceutically acceptable carrier.

In some other embodiments, the invention relates to a method of prolonging healthspan, lifespan and/or mental acuity of a subject, comprising administering to the subject an effective amount of a compound of Formula I (or a pharmaceutically acceptable salt, solvate or prodrug thereof). The invention also relates to the use of a compound of Formula I (or a pharmaceutically acceptable salt, solvate or prodrug thereof) as a medicament for extending life expectancy and/or reducing aging or an age-related illness or symptom. In addition, the invention relates to a pharmaceutical composition for a treatment of extending life expectancy comprising a therapeutically effective amount of a compound of Formula I (or a pharmaceutically acceptable salt, solvate or prodrug thereof), together with a pharmaceutically acceptable carrier.

In some further embodiments, the invention relates to a long-term method of increasing and/or improving healthspan, lifespan, and/or mental acuity of a subject, wherein said method comprises administering a therapeutically effective amount of a compound of Formula I (or a pharmaceutically acceptable salt, solvate or prodrug thereof), wherein the administration of the compound is at least for 1, 2, 3, 4, 5, 6, 7, 8, 9 or 10 years. With such a method, the lifespan, healthspan, mental acuity and/or healthy aging of the subject is preferably extended, improved or promoted by up to about 10%, 20%, 30%, 40%, 50%, 60%, or 70% as compared to untreated control subjects.

Examples of age-related illnesses and symptoms include, but are not limited to cardiovascular disease, a metabolic syndrome, a bone-loss disorder, a neurodegenerative disease, pre-diabetes, diabetes, obesity, osteoporosis, coronary artery disease, cerebrovascular disease, heart attack, stroke, peripheral arterial disease, aortic valve disease, stroke, mild cognitive impairment, pre-dementia, dementia, macular degeneration, and cataracts, hair thinning, hair graying, loss of mobility, loss of stamina, fatigue, increased susceptibility to infection, a metabolic change, a biochemical change, cardiac hypertrophy, heart failure, myocardial infarction, ischemia reperfusion injury, inflammatory disease, proinflammatory states, arthropathies, autoimmune diseases, and/or Alzheimer's disease (AD), Parkinson's disease (PD) Huntington's Disease, Frontotemporal Dementia, Pick's Disease, Gaucher's Disease and Amyotrophic Lateral Sclerosis (i.e., Lou Gehrig's Disease).

In the methods of the invention, the compound may be administered to the subject in a daily dosage of from about 20-500 mg/day, 50-150 mg/day, 50-200 mg/day, 50-250 mg/day, 250-500 mg/day, or 250 mg-1500 mg/day. Higher or lower doses are also contemplated as it may be necessary to use dosages outside these ranges in some cases. The daily dosage may be divided, such as being divided equally into two to four times per day daily dosing. Moreover, for long-term administration, as might be required in a method of inducing increasing and/or improving healthspan, lifespan, and/or mental acuity of a subject, the compound may, preferably, be administered at a dose of approximately 50 mg/day, 75 mg/day, 100 mg/day, 150 mg/day, 200 mg/day 250 mg/day, 300 mg/day, 350 mg/day, 400 mg/day, 450 mg/day, 500 mg/day, 550 mg/day, 600 mg/day, 650 mg/day, 700 mg/day, 750 mg/day, 800 mg/day, 850 mg/day, 900 mg/day, 950 mg/day, 1000 mg/day, 1050 mg/day, 1100 mg/day, 1150 mg/day, 1200 mg/day, 1250 mg/day, 1300 mg/day, 1350 mg/day, or between 50-150 mg/day, 50-200 mg/day, 50-250 mg/day, 250-500 mg/day, 250-1000 mg/day, 1000-1500 mg/day, 1500-2000 mg/day, or 1000-2000 mg/day, or less than 1000 mg/day, or approximately 1 mg/kg/day, 2 mg/kg/day, 3 mg/kg/day, 4 mg/kg/day, 5 mg/kg/day, 6 mg/kg/day, 7 mg/kg/day, 8 mg/kg/day, 9 mg/kg/day, 10 mg/kg/day, 11 mg/kg/day, 12 mg/kg/day, and/or between 4-12 mg/kg/day.

In some preferred embodiments, the methods of the invention may be particularly applied to subjects including humans suffering from pain associated with acute sore throat, human suffering from bronchopulmonary diseases associated with the production of excess and/or highly viscous mucus, humans suffering from a lysosomal storage disorder (LSD) such as Gaucher's Disease, and neurological diseases and conditions such as Parkinsonism (including PD and Dementia with Lewy Bodies), AD, ALS, HD, Pick's Disease, Gaucher's Disease and/or Frontotemporal Dementia (FTD).

Parkinson's Disease and Other Diseases Involving Dysfunctional Autophagy

Ambroxol (and ambroxol hydrochloride and bromhexine) as well as the analogs of ambroxol of the invention may be particularly applied to the treatment of aging-associated diseases involving dysfunction of proteolysis/lysosomes, autophagy and chronic inflammation, such as Alzheimer's disease (AD), Parkinson's disease (PD) Huntington's Disease, Frontotemporal Dementia, Pick's Disease, Gaucher's Disease and Amyotrophic Lateral Sclerosis (ALS) (i.e., Lou Gehrig's Disease).

As mentioned above, the ability of ambroxol to increase the activity of GCase may be beneficial for the treatment of PD in individuals with loss-of-function mutations in the glucocerebrosidase gene, GBA1, (McNeill A et al., 2014 supra), which are prime hereditable risk factors for PD (Do J et al., Neurodegener 14:36, 2019). Enhanced GCase activity resulting from ambroxol treatment is expected to increase the degradative capacity of lysosomes, aiding in the clearance of intracellular aggregated α-synuclein (aSyn), a protein implicated in the pathogenesis of PD (Migdalska-Richards A et al., 2016 supra). GCase deficiency is also associated with lysosomal and mitochondrial dysfunction observed in PD (Brooker and Krainc, 2021 Essays in Biochemistry, 65(7), pp. 873-883), which may partially explain ambroxol's improvements to lysosome and mitochondrial function (Magalhaes et al., 2018 Scientific Reports, 8(1), p. 1385). Based on this and promising preclinical data, the use of ambroxol is under investigation in clinical trials as a disease modifying compound for PD (see, for example, Silveira C R A et al., BMC Neurol 19:20, 2019, and Mullin S et al., JAMA Neurol 77:427-434, 2020) and the lipid storage disorder Gaucher's disease (Zimran, Altarescu and Elstein, 2013 Blood Cells, Molecules & Diseases, 50(2), pp.

134-137; Narita et al., 2016 Annals of Clinical and Translational Neurology, 3(3), pp. 200-215).

However, the potentially beneficial biological activities of ambroxol are known to extend well beyond its chaperoning of GCase. In particular, ambroxol exerts extensive effects on the autophagic endolysosomal network (AELN) (McNeill et al., 2014 Brain: A Journal of Neurology, 137(Pt 5), pp. 1481-1495; Fois et al., 2015 Cell Calcium, 58(6), pp. 628-637; Magalhaes et al., 2018 supra), evoked immune response (Beeh et al., 2008 European Journal of Medical Research, 13(12), pp. 557-562; Kern and Schwickert, 2017 Journal of Pain Research, 10, pp. 1905-1929), and block of channels involved in chronic pain (Russo et al., 2022 Pain [Preprint]. Available at: doi.org/10.1097/j.pain.0000000000002693). As such, ambroxol could potentially prove useful for the treatment of myriad diseases with defects in the AELN, immune system, or nociception as core features. As examples, many neurodegenerative disorders, including PD, FTD, ALS, HD and AD, exhibit deficits in production or degradation of neurotoxic protein species within the AELN which can in turn drive a chronic inflammatory milieu in brain tissue.

Several of the mechanisms by which ambroxol exerts its impact on cellular processes have been elucidated. Ambroxol is an amphipathic amine which readily crosses the cellular membrane via passive diffusion allowing it to directly access the intra-cellular and -organellar space. Within the cell, ambroxol acts as a weak base that becomes protonated and trapped in acidic subcellular compartments including lysosomes and other structures of the late endo-lysosomal pathway (Magalhaes J et al., 2018 supra; and Fois G et al., 2015 supra). These properties explain ambroxol's high bioavailability and tendency to accumulate in lipid-rich organ systems such as the brain, lungs, and skin (Mullin S et al., 2020 supra). Within the cytoplasm, ambroxol also acts as a potent scavenger and stabilizer of free radicals produced in the course of cellular metabolism and as part of the innate immune response (Stetinová, Herout and Kvetina, 2004 Clinical and Experimental Medicine, 4(3), pp. 152-158). Finally, ambroxol has been shown to impart analgesia by directly blocking Nav1.7/8 channels associated with neuropathic pain (Kern and Schwickert, 2017 supra).

Amphipathic trapping of ambroxolin acidic compartments exerts influence over the AENL system in several ways. One important consequence of the protonation of ambroxol in lysosomes is the resultant deacidification of the lysosomal lumen (Mullin S et al., 2020 supra, and Lu S et al., PloS One 12:eo173771, 2017). This process mobilizes intraorganellar calcium stores which result in the activation of lysosome-associated transcription factor EB (TFEB). Activated TFEB relocalizes to the nucleus where it initializes transcription of a gene network with master regulatory control over lysosomal biogenesis (Medina D L et al., Nat Cell Biol 17:288-299, 2015). Upregulation of this gene network results in increased cellular capacity to degrade long-lived proteins (Sardiello et al., 2009 Science, 325 (5939), pp. 473-477), particularly proteins associated with neurodegenerative disorders such as hyperphosphorylated tau (Martini-Stoica et al., 2018 The Journal of Experimental Medicine, 215(9), pp. 2355-2377). Ambroxol effectively activates TFEB both in cell culture as well as in vivo. In cultures derived from brain (Magalhaes et al., 2018 supra), skin (McNeill et al., 2014 supra), or immune-related tissues (Choi et al., 2018 Antimicrobial Agents and Chemotherapy, 62(9)) application of ambroxol results in upregulation of TFEB at the transcription, protein, and/or activation levels. Increase TFEB activity drives expression of multiple lysosomal enzymes including the protease Cathepsin D which is known to degrade alpha synuclein, beta amyloid and tau. See, e.g., Suire, C. N. et al. "Cathepsin D: A Candidate Link between Amyloid β-protein and Tauopathy in Alzheimer Disease" J Exp Neurology 2, 10-15 (2021); Sevlever, D. et al., "Cathepsin D Is the Main Lysosomal Enzyme Involved in the Degradation of α-Synuclein and Generation of Its Carboxy-Terminally Truncated Species," Biochemistry-US 47, 9678-9687 (2008).

Relatedly, ambroxol in a high dose regime can drive cellular autophagy into a secretory regime (see, for example, McNeill A et al., 2014 supra, and Silveira C R A et al., 2019 supra). Secretory autophagy comprises the mechanisms by which normally functioning and defective proteins are packaged into membrane-bound organelles termed autophagosomes and secreted extracellularly, and represents an alternative process to degradative autophagy in which the autophagosome fuses with a lysosome to drive breakdown and recycling of autophagosomal contents (Rabouille C et al., J Cell Sci 125:5251-5255, 2012). Upregulation of autophagy-dependent secretion is recognized as a potential route for disease modification in neurodegenerative disorders (Ponpuak M et al., Curr Opin Cell Biol 35:106-116, 2015).

In the case of PD, as well as AD, aggregation-prone proteins aSyn (in PD; see, for example, Dehay B et al., J Neurosci Off J Soc Neurosci 30:12535-12544, 2010) and beta amyloid (in AD; see, for example, Vickers J C et al., Exp Neurol 141:1-11, 1996) form degradation-resistant inclusions that accumulate in autophagic vacuoles. In both cases, protein aggregates drive dysregulation at multiple points along the cellular autophagic processing pathways which may potentially be relieved by secretory unloading.

Ambroxol is capable of directly engaging the secretory autophagic system. In primary neuronal cultures from cells engineered to express PD pathology and unmodified counterparts, ambroxol enhances secretion of aSyn while clearing intracellular stores of aggregation-prone versions of this protein (Magalhaes J et al., 2018 supra). These results extend further to AD's pathology, where clearance of intracellular aggregation-prone tau is driven by the application of bromhexine to brain-derived cell culture (Chauhan S et al., Nat Commun 6:8620, 2015). Taken together, these data indicate that ambroxol exerts beneficial effects on the AELN by increasing innate cellular degradative capacity while unloading toxic protein aggregates from cells such as neurons that possess lower innate degradative capabilities.

Another important system for human health ambroxol influences is the immune response. Epidemiological and preclinical work has indicated that driving the immune response away from an innate inflammatory response into an anti-inflammatory/adaptive state may be beneficial for multiple chronic disease states. For example, in many neurodegenerative disorders, longitudinal sampling of patient sera and cerebrospinal fluid indicate a progressive increase of inflammatory response markers, such as cytokines including interleukin 1β, 6, 8, and tissue necrosis factor alpha, and activation of the NOD-, LRR- and pyrin domain-containing protein 3 (NLRP3)-associated inflammasome that mirrors loss of cognitive function (Heneka et al., 2015 The Lancet. Neurology, 14(4), pp. 388-405; Wang, Liu and Zhou, 2015 Translational Neurodegeneration, 4, p. 19). Concordantly, variants of many genes with innate immune regulatory function are associated with increased risk of AD and PD (Hollingworth et al., 2011 Nature Genetics, 43(5), pp. 429-435; Griciuc and Tanzi, 2021 Current Opinion in Neurology, 34(2), pp. 228-236). In contrast, upregulation of markers of anti-inflammation and adaptive immunity such as interferon gamma and interleukin 12 correlates with decreased incidence of AD in elderly adults (Yang et al., 2022 Alzheimer's & Dementia, 18(4), pp. 645-653).

Neurodegenerative disorders are emblematic of chronic inflammatory states that arise when the immune system is unable to alleviate the source of immune challenge over a chronic timeframe. In the case of neurodegenerative disorders, these immune insults may in part be provided by toxic aggregated proteins produced largely by cells within the brain. Chronic inflammation can also occur in the context of infection that persists in the body such as mycoplasma pneumonia and inappropriate immune activation by self-derived antigens.

With respect to inflammation, ambroxol has also been shown to profoundly reshape the immune response to both pathogenic and self-derived threats. Studies across multiple organ systems, particularly the brain (Jiang et al., 2020 BioMed Research International, 2020, p. e8131286), lungs (Takeda et al., 2016 Immune Network, 16(3), pp. 165-175; Zhang et al., 2016; Kókai et al., 2021 Microorganisms, 9(4), p. 880), and gut (Schneider et al., 2021 EMBO Molecular Medicine, 13(1), p. e12724; Cavalu et al., 2022 The FASEB Journal, 36(9), p. e22496.) have confirmed that ambroxol acts to reduce pro-inflammatory response to such threats while preserving the adaptive aspects of immune response. In particular, ambroxol has been shown to decrease expression of pro-inflammatory cytokines such as interleukins 1β, 6, 8, 10, and tissue necrosis factor-α (Bianchi et al., 1990 Agents and Actions, 31(3-4), pp. 275-279; Jang et al., 2003 Pharmacology & Toxicology, 92(4), pp. 173-179; Wang et al., 2011; Zhongguo Ying Yong, et. al., Chinese Journal of Applied Physiology, 27(2), pp. 231-235) as well as reductions in pathways upstream of inflammasome activation such as Nuclear Factor kappa B (NF-κB) (Cavalu et al., 2022 supra). This suppression is due at least in part to ambroxol's ability to scavenge free radicals (Peroni et al., 2013 International Journal of Immunopathology and Pharmacology, 26(4), pp. 883-887) and may also involve direct block of specific inflammation-associated channels (Schneider et al., 2021 supra).

Unlike non-specific immune suppressing agents such as non-steroidal anti-inflammatory drugs, ambroxol preserves and in some cases enhances aspects of the anti-inflammatory and adaptive immune system. This includes the upregulation of anti-inflammatory cytokines interleukins 10 and 12 as well as adaptive immune-associated interferon-γ in lung tissue in response to pathogen and ovalbumin challenge (Takeda et al., 2016 supra; Kokai et al., 2021 supra). These immune effectors may explain ambroxol's long-known clinical benefit in chronic respiratory diseases such as chronic obstructive pulmonary disorder (Plomer and de Zeeuw, 2017 MMW Fortschritte der Medizin, 159(Suppl 5), pp. 22-33). Additionally, they may account for preclinical observations of reduced inflammation in models of ulcerative colitis (Schneider et al., 2021 supra) and reduced microglial activation in a model of intracerebral hemorrhage (Jiang et al., 2020 supra).

It is likely that the anti-inflammatory effects described above are related to ambroxol's impacts on autophagy. Autophagy has been noted to have a key role in regulating immune response. Particularly, activation of TFEB function drives degradation of key mediators of inflammation including inflammasome components such as NLRP3 and apoptosis-associated speck-like protein containing a caspase-recruitment domain (ASC) (Shi et al., Nature Immunology, 13(3), pp. 255-263 (2012); Deretic, Immunity, 54(3), pp. 437-453 (2021). Inflammasome inactivation through degradation results in dampened inflammatory response including reduction in production and release of pro-inflammatory cytokines such as IL-1β. It is thus probable that ambroxol's immune modulatory function lies downstream of its effect on autophagy.

Ambroxol also possesses potent analgesic properties. Mechanistically, this effect is attributed to ambroxol's ability to block voltage-dependent sodium channels including Nav1.7 (Leffler, Reckzeh and Nau, 2010 European Journal of Pharmacology, 630(1-3), pp. 19-28) and 1.8 (Weiser and Wilson, 2002 Molecular Pharmacology, 62(3), pp. 433-438) which are preferentially expressed by neurons involved in nociception (Bennett et al., 2019 Physiological Reviews, 99(2), pp. 1079-1151). This mechanism at least partially explains ambroxol's classic use as a treatment for moderate to severe pain associated with acute sore throat (Fischer et al., 2002 Arzneimittel-Forschung, 52(4), pp. 256-263). It additionally has increased interest in the use of ambroxol for the treatment of neuropathic pain (Russo et al., 2022 supra).

Moreover, a recently discovered way cells regulate TFEB nuclear access and transcriptional function is poly(ADP-ribosyl)ation (PARsylation) (Kim et al., 2021; Chen et al., 2024). Parsylation is a reversible post-translational modification process where poly(ADP-ribose) polymerases (PARPs) catalyze the transfer of ADP-ribose units to target proteins. This modification serves to recruit E3 ligase ubiquitination of the target protein, with the end result of increasing turnover through the ubiquitin proteasome system (Vivelo et al., 2019).

In the case of TFEB, PARsylation drives nuclear localization in a phospho-state-independent manner. As expected, nuclear localization augments TFEB-initiated transcription, but with a major caveat. In the PARsylated state, TFEB complexes with Wnt/beta-catenin, resulting in transcriptional initiation of a gene set that is entirely distinct from the CLEAR network (Kim et al., 2021). In essence, PARsylation allows TFEB to flexibly change the proteins it turns on based on the moment-by-moment needs of the cell.

Multiple hard-to-explain observations in brain cells treated with ambroxol may be explainable if ambroxol engages Wnt/beta-catenin pathway regulation by TFEB. For example, following a stroke in a mouse model (dMCAO paradigm), ambroxol causes cells born from the proliferative zone of the brain (called the subventricular zone) to preferentially differentiate into new neurons rather than the more-typical reactive astrocyte. In a parallel in vitro model (oxygen glucose deprivation of iPSCs), the authors show that ambroxol increases beta-catenin signaling as well as GCase (Ge et al., 2021). This fits with expected effects where Wnt/beta-catenin transcriptional regulation tends to cause neuroprogenitor cells to assume a neural rather than glial fate (Gao et al., 2021; Kriska et al., 2021).

Other studies support a connection between ambroxol and Wnt/beta-catenin mediated via TFEB. One study demonstrated a link between GCase and Wnt/beta-catenin transcriptional regulation. In an iPSC line induced to dopaminergic fate, GD mutations drive reduced Wnt/beta-catenin signaling. Addition of recombinant GCase brought the Wnt/beta-catenin signaling back up to wild type levels (Awad et al., 2017).

Thus, in conclusion, and while not wishing to be bound by theory, it is considered that the abovementioned observations indicate that the analogs described herein, like ambroxol, may increase degradation and/or secretion of toxic intracellular proteins, protein fragments, misfolded proteins, protein aggregates or debris associated with disorders of the AELN. These analogs could further modulate immune response to a less inflammatory state likely through scavenging of free radicals and interactions with inflammation-associated channels. Finally, the described analogs may block channels upregulated in disease states characterized by chronic pain.

Implications—The ambroxol analogs described herein, offer considerable potential as an effective treatment of neurological diseases and conditions such as PD, AD and other aging-associated diseases involving dysfunction of autophagy), by enabling the secretion of toxic aggregated proteins (e.g., aggregated aSyn, beta amyloid and tau protein) from affected cells despite autophagy dysfunction, and by maintaining organelle health.

In some cases, it may be advantageous to administer the ambroxol analogs described herein with an agent intended for, for example, the prevention and/or removal of toxic aggregated proteins.

Thus, in another aspect of the invention, a method is provided for preventing, reducing the symptoms of and/or stabilizing the progression of Alzheimer's disease (AD) or other diseases associated with pathological protein misfolding, aggregation and deposition (including Parkinson's disease (PD), Huntington's disease (HD), Amyotrophic Lateral Sclerosis (ALS) (i.e., Lou Gehrig's Disease), Pick's Disease, Gaucher's Disease and Frontotemporal degeneration (FTD)) in a subject, said method comprising administering to the subject an effective amount of ambroxol (or a related compound such as ambroxol hydrochloride and bromhexine) or an analog of the invention in combination with one or more suitable anti-beta amyloid antibody or fragment thereof. Such a combination therapy may produce, for example, a synergistic effect in removing aggregated beta amyloid associated with, for example, AD.

The ambroxol analogs and an anti-beta amyloid antibody or fragment thereof may be administered, for example, as part of the same treatment protocol even though administered as separate compositions. Here, the ambroxol analog and the anti-beta amyloid antibody or fragment thereof may be administered simultaneously or sequentially in any order (e.g., within seconds or minutes or even hours (e.g., 2 to 48 hours)).

The anti-beta amyloid antibody or fragment thereof may be selected from those known to those skilled in the art. Suitable antibodies may include human or humanized anti-Aβ3 monoclonal antibodies of the group consisting of Bapineuzumab (Pfizer Inc./Janssen Pharmaceuticals, Inc.), Solanezumab (Eli Lilly and Company), Gantenerumab (Hoffman-La Roche), Crenezumab (Genentech, Inc.), Ponezumab (Pfizer Inc.), Donanemab (Eli Lilly), BAN2401/Lecanamab (BioArctic Neuroscience, AB/Eisai Co., Ltd/Biogen, Inc.) and Aducanumab (Aduhelm™ Biogen, Inc.) (see also, van Dyck C H., Biol Psychiatry 83(4):311-319, 2018). Suitable antibody fragments may include fragments such as Fab fragments and scFv antibodies targeted to Aβ3 including scFv molecules described by Sebollela A., J Neurochem 142(6):934-937, 2017, and Zha J et al., Scientific Reports 6:36631, 2016.

In some embodiments, the method is to be operated for the prevention of, reduction of symptoms of, and/or for slowing the progression of, AD or other diseases associated with pathological protein misfolding, aggregation and deposition (including Parkinson's disease (PD), Huntington's disease (HD)), Amyotrophic Lateral Sclerosis (ALS) (i.e., Lou Gehrig's Disease), Pick's Disease, Gaucher's Disease and Frontotemporal degeneration (FTD)). Thus, the method may, for example, prevent the occurrence, development or progression of the disease or condition, or the occurrence, development or progression of one or more symptom or deleterious characteristic of the disease or condition (e.g., the toxic aggregation of Aβ proteins). Aggregation of beta amyloid and tau are known to appear early in the development of Alzheimer's disease, so a therapeutic method intended to prevent and/or remove toxic aggregates of Aβ3 or tau, as may be achieved by administering ambroxol (or related compound) or analog of the invention, offers significant potential.

In a variation, the invention may provide a method for the prevention of, reduction of symptoms of, and/or for slowing the progression of, AD or other diseases associated with pathological protein misfolding, aggregation and deposition (including Parkinson's disease (PD), Huntington's disease (HD), Amyotrophic Lateral Sclerosis (ALS) (i.e., Lou Gehrig's Disease), Pick's Disease, Gaucher's Disease and Frontotemporal degeneration (FTD)), comprising administering to the subject an effective amount of ambroxol (or a related compound such as ambroxol hydrochloride and bromhexine) or an analog of the invention. That is, the ambroxol or related compound or analog of the invention may be used as the sole active agent.

In some embodiments of the methods for the prevention of, reduction of symptoms of, and/or the slowing of the progression of, AD or other diseases associated with pathological protein misfolding, aggregation and deposition (including Parkinson's disease (PD), Huntington's disease (HD), Amyotrophic Lateral Sclerosis (ALS) (i.e., Lou Gehrig's Disease), Pick's Disease, Gaucher's Disease and Frontotemporal degeneration (FTD)), the subject may be selected on the basis of a suitable biomarker indicative of an at-risk patient or patient in an early stage of development of AD or other diseases associated with pathological protein misfolding, aggregation and deposition (including Parkinson's disease (PD), Huntington's disease (HD), Amyotrophic Lateral Sclerosis (ALS) (i.e., Lou Gehrig's Disease), Pick's Disease, Gaucher's Disease and Frontotemporal degeneration (FTD)). For AD, the biomarker levels may be found the CSF and/or blood early or in preclinical stage(s) of AD. See, for example, Janelidze, S. et al., "Plasma P-tau181 in Alzheimer's Disease: Relationship to Other Biomarkers, Differential Diagnosis, Neuropathology and Longitudinal Progression to Alzheimer's Dementia," Nat Med 26:379-386; see, also Hansson et al., "The Alzheimer's Association appropriate use recommendations for blood biomarkers in Alzheimer's disease," Alzheimer's & Dementia: 2669-2686 (2022)). Thus, in one example, the methods may further comprise selecting the subject by assaying for an increased level of phosphorylated tau proteins (p-tau) p-tau217 (i.e. tau phosphorylated at the Thr-217 residue) (Palmquvist et al., "Discriminative Accuracy of Plasma Phospho-tau217 for Alzheimer Disease vs Other Neurodegenerative Disorders" JAMA 324:772-781 (2020)) or p-tau181 (i.e. tau phosphorylated at the Thr-181 residue) (Janelidze et al., "Plasma P-tau181 In Alzheimer's Disease: Relationship To Other Biomarkers, Differential Diagnosis, Neuropathology And Longitudinal Progression To Alzheimer's Dementia," Nat Med 26:379-386 (2020)), or oligomerized species of amyloid β (Shea et al., "SOBA: Development and Testing Of A Soluble Oligomer Binding Assay For Detection Of Amyloidogenic Toxic Oligomers" Proceedings of the National Academy of Sciences 119:e2213157119 (2022)) in a suitable sample (e.g. a sample of CSF, whole blood or plasma). These biomarkers can accurately differentiate memory patients classified as cognitively unimpaired, mildly cognitively impaired, or AD dementia sufferers, and moreover, it has been shown that the these biomarkers accurately predict which patients will progress to AD dementia (Janelidze et al., 2020; Palmqvist et al., "Prediction Of Future Alzheimer's Disease Dementia Using Plasma Phospho-Tau Combined With Other Accessible Measures," Nat Med 27:1034-1042 (2021); Shea et al., 2022) Jia J., et al. "Biomarker Changes during 20 Years Preceding Alzheimer's Disease," New England Journal of Medicine, Volume 390, No. 8, pp 712-722 (2024)). These same species may be monitored longitudinally in treatment subjects to assess impact of treatment. Other p-tau tau isoforms may be assayed as well, such as p-tau231 (Ashton, N. J. et al. Acta Neuropathol 1-16 (2021)) or p-tau235 (Lantero-Rodriguez, J. et al. Embo Mol Med 13, e15098 (2021)). Other potential biomarkers include glucose metabolism, or aggregated proteins such as beta amyloid or Tau measured by Positron Emission Tomography (PET)(Therriault, J. et al. Nat Aging 1-10 (2022) doi: 10.1038/s43587-022-00204-0. Iaccarino, L., et al. "Journal of Alzheimer's Disease, 59, pp 603-614 (2017).) Retinal-imaging based biomarkers including amyloid deposition and thinning of the nerve fiber layer and could also be used for the early diagnosis of AD (Snyder, P. J. et al. Alzheimers Dement. Diagn. Assess. Dis. Monit. 4, 169-178 (2016); Koronyo, Y. et al. JCI Insight 2, (2017)).

Other suitable biomarkers indicative of an at-risk patient or patient in an early stage of development of AD or other amyloidoses include, for example, e4 allele of the ApoE gene, Apolipoprotein E prototype ($C_2N$ Diagnostics), the pyroglutamate-modified amyloid β protein, N3pG, pTau217, and/or amyloid beta 42/40 ratio (Aβ 42/40)($C_2N$ Diagnostics). Plasma NFL (Neurofilament light chain) is elevated in many neurodegenerative diseases. It is not specific to any specific neurodegenerative diseases, and instead reflects disease activity and severity. For example it is elevated in Multiple Sclerosis patients who have active ongoing demyelination, but drops when the patients are treated with immunosuppressants (Barro, C. & Zetterberg, H. Acta Neurol Scand (2021) doi:10.1111/ane.13415). Plasma exosomes bearing neuronal proteins also appear promising biomarkers to diagnose a number of neurodegenerative diseases, including Parksinon's disease, Alzheimer's disease, and head injury (Rastogi, S. et al. Int J Mol Sci 22,440 (2021)).

Examples of additional marker that have been used to identify patients at risk include for example, Roche's Elecsys AD (Ab42, Ab40, p-tau181, and total tau) or Fujirebio's beta-amyloid ratio test (e.g., Ab42 and Ab40), Eli Lilly's Tauvid (flourtaucipir-detecting tau on PET) or Amyvid (florbetapir, detecting amyloid on PET), or Neuraceq (fluorbetapen) or Vizamyl (flutemetamol).

In some embodiments of the methods for the prevention of, reduction of symptoms of, and/or the slowing of the progression of, AD or other diseases associated with pathological protein misfolding, aggregation and deposition (including Parkinson's disease (PD), Huntington's disease (HD), Amyotrophic Lateral Sclerosis (ALS) (i.e., Lou Gehrig's Disease), Pick's Disease, Gaucher's Disease and Frontotemporal degeneration (FTD)), the subject may be selected on the basis of genotyping of at least one gene or locus indicative of a patient at-risk of AD or other diseases associated with pathological protein misfolding, aggregation and deposition (including Parkinson's disease (PD), Huntington's disease (HD), Amyotrophic Lateral Sclerosis (ALS) (i.e., Lou Gehrig's Disease), Pick's Disease, Gaucher's Disease and Frontotemporal degeneration (FTD)). For AD, the genotyping may be of the gene encoding apolipoprotein E (ApoE); subjects carrying the ε4 allele of ApoE are at increased risk of AD compared with those carrying the more common ε3 allele, whereas the e2 allele decreases risk (Liu C-C et al., Nat Rev Neurol. 9(2):106-118, 2013). Suitable methodologies for conducting ApoE genotyping are known to those skilled in the art and include, for example, suitable RT-PCR protocols (see, for example, Zhong L et al., Mol Neurodegener. 11:2, 2016). However, in other embodiments, the subject may be selected on the basis of genotyping of p-tau217, p-tau181 and/or N3pG.

In some embodiments of the methods for preventing and/or treating Alzheimer's disease (AD) or other diseases associated with pathological protein misfolding, aggregation and deposition (including Parkinson's disease (PD), Huntington's disease (HD), Amyotrophic Lateral Sclerosis (ALS) (i.e., Lou Gehrig's Disease), Pick's Disease, Gaucher's Disease and Frontotemporal degeneration (FTD)), it may be preferred that the ambroxol (or related compound) or analog of the invention is administered to the subject in a relatively high daily dosage selected from a dosage that: (i) provides a peak concentration in serum of the subject that is greater than 1 μM such as, for example, 2-50 μM, 2-25 μM or 10-20 μM;

(ii) provides a peak concentration in brain tissue of the subject that is greater than 3 μM such as, for example, 5-50 μM, 5-25 μM or 10-20 μM; or (iii) is in the range of about 250 mg-1000 mg/day or 750-1000 mg/day;

since such a high daily dose may be necessary to enable the ambroxol (or related compound) or analog of the invention to upregulate the secretion of toxic aggregated proteins (e.g., aggregated Aβ) from affected cells.

Pharmaceutical Compositions

In an aspect, the invention includes a composition comprising a therapeutically effective amount of a compound of Formula I (for example, a compound as shown in FIG. 1) or a pharmaceutically acceptable salt, solvate or prodrug thereof, in conjunction with a pharmaceutically acceptable carrier for preventing and/or treating various diseases and medical conditions in a subject including respiratory diseases and conditions, lysosomal storage disorders (LSDs), and neurological diseases and conditions, or for extending life expectancy of a subject. For example, a composition comprising a compound of Formula I (or a pharmaceutically acceptable salt, solvate or prodrug thereof) may be used for (a) treating, inhibiting, or reducing aging of a subject, (b) treating, inhibiting, or reducing an age-related symptom or an age-related disease in a subject, and/or (c) increasing the healthspan, lifespan, and/or mental acuity of a subject.

The compound of Formula I (or a pharmaceutically acceptable salt, solvate or prodrug thereof) may be administered in the form of a pharmaceutical composition, in combination with a pharmaceutically acceptable carrier. In such compositions, the compound of Formula I may comprise from 0.1 to 99.99 weight percent.

The compound of Formula I is preferably administered with a pharmaceutically acceptable carrier selected on the basis of the selected route of administration and standard pharmaceutical practice. The compound of Formula I may be formulated into dosage forms according to standard practices in the field of pharmaceutical preparations. See Alphonso Gennaro, ed., Remington's Pharmaceutical Sciences, $18^{th}$ Edition (1990), Mack Publishing Co., Easton, Pa. Suitable dosage forms may comprise, for example, tablets, capsules, solutions, parenteral solutions, troches, suppositories, or suspensions. Suitable examples of the preparation of oral, topical, suppository and parenteral formulations of ambroxol, bromhexine, or other ambroxol derivatives, which may be readily adapted for compounds of the present invention, are disclosed in, for example, Examples 1-8 of WO 2005/007146, or its equivalent US 2005/00148747, incorporated herein by reference.

In another aspect, the invention provides the use of a compound of Formula I in the preparation of a medicament for preventing and/or treating various diseases and medical conditions in a subject including respiratory diseases and conditions, lysosomal storage disorders (LSDs), and neurological diseases and conditions, or for extending life expectancy of a subject.

For parenteral administration, the compound of Formula I may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol, or with a plant extract as a supplement. Solutions for parenteral administration preferably contain a water-soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

For oral administration, the compound of Formula I (or a pharmaceutically acceptable salt, solvate or prodrug thereof) may be combined with one or more solid inactive ingredients for the preparation of tablets, capsules, pills, powders, granules or other suitable oral dosage forms. For example, the compound of Formula I may be combined with at least one excipient such as fillers, binders, humectants, disintegrating agents, solution retarders, absorption accelerators, wetting agents, absorbents or lubricating agents. According to one tablet embodiment, the compound of Formula I may be combined with carboxymethylcellulose calcium, magnesium stearate, mannitol and starch, and then formed into tablets by conventional tableting methods.

For oral administration, the compound of Formula I (or a pharmaceutically acceptable salt, solvate or prodrug thereof) may be provided in a liquid oral pharmaceutical composition. Liquid oral dosage forms can offer unique advantages over solid dosage forms like tablets and capsules. For example, in many instances, the amount of active ingredient necessary to treat a specific disease or condition requires multiple tablets or capsules one or more times a day. The ingestion of multiple tablets or capsules includes not only the active pharmaceutical ingredient, but multiple doses of excipients which are used to formulate the tablets and capsules. Such excipients, such as oils and alcohols, are typically not well tolerated by many patients and commonly lead to gastric distress. Additionally, liquid oral dosage forms are more patient compliant than solid dosage forms since delivery of the active pharmaceutical ingredient is achieved in only one or two doses per day. Further, liquid oral dosage forms provide rapid absorption of an active pharmaceutical ingredient from the gastro-intestinal tract. Moreover, liquid oral dosage forms allow the use of flavoring and/or palatability agents, which further promotes patient acceptance and compliance.

Accordingly, in some preferred embodiments, the composition of the invention will be a liquid oral pharmaceutical composition. Such a composition may be particularly suited for preventing and/or treating a lysosomal storage disorder (LSD) such as Gaucher's disease, or a neurological disease or condition such as PD. In some embodiments, the composition will comprise a "high loading" of the compound of Formula I (or a pharmaceutically acceptable salt, solvate or prodrug thereof) in order to deliver an effective amount in a small volume (e.g., 15 mL dose, one, two or more times a day). A high drug loading liquid oral pharmaceutical composition according to the invention may provide at least one of the following advantages: (i) improved absorption in the gastrointestinal tract; (2) maintain effective blood concentration over a 24 hour period; (3) reduced undesirable side effects of excipients as compared to solid dosage forms; (4) a reduction in the number of doses required; and (5) an improved taste and mouthfeel qualities.

In one specific embodiment of a high drug loading liquid oral pharmaceutical composition of the invention, the composition comprises (i) a compound of Formula I (or a pharmaceutically acceptable salt, solvate or prodrug thereof); and (ii) at least one pharmaceutically acceptable excipient, wherein the compound of Formula I (or a pharmaceutically acceptable salt, solvate or prodrug thereof) is in the form of granules having a granular core comprising from about 60 to about 97 weight percent of an active pharmaceutical ingredient and from about 3 to about 40 weight percent of the excipient, wherein the weight percent is based on the total weight of the granular core.

In another specific embodiment of a high drug loading liquid oral pharmaceutical composition of the invention, the composition comprises (i) a compound of Formula I (or a pharmaceutically acceptable salt, solvate or prodrug thereof); (ii) at least one pharmaceutically acceptable excipient; and (iii) a diluent, wherein the compound of Formula I (or a pharmaceutically acceptable salt, solvate or prodrug thereof) is in the form of granules having a granular core comprising from about 60 to about 97 weight percent of an active pharmaceutical ingredient and from about 3 to about 40 weight percent of the excipient, wherein the weight percent is based on the total weight of the granular core; wherein the granule core is coated with (iv) a water-soluble seal coating in an amount to provide from about 0.5 to about 5 percent weight gain, and (v) an enteric coating in an amount to provide from about 0.5 to about 50 percent weight gain.

Such high drug loading liquid oral pharmaceutical compositions may be prepared by a method comprising, for example: (a) preparing granules having a granular core comprising from about 60 to about 97 weight percent of a compound of Formula I (or a pharmaceutically acceptable salt, solvate or prodrug thereof) and from about 3 to about 40 weight percent of at least one pharmaceutically acceptable excipient, wherein the weight percent is based on the total weight of the granular core; (b) coating the granules with a water-soluble seal coating in an amount to provide from about 0.5 to about 5 percent weight gain; (c) coating the granules prepared in step (b) with an enteric coating in an amount to provide from about 0.5 to about 50 percent weight gain; and (d) preparing a liquid suspension comprising the enteric coated granules prepared in step (c) and a liquid suspension formulation, wherein the liquid suspension formulation comprises a suspending agent, a vehicle to enhance the stability of the high drug loading liquid oral pharmaceutical composition, and a diluent.

The compound of Formula I (or a pharmaceutically acceptable salt, solvate or prodrug thereof) is preferably in the form of granules which preferably, after micronizing, have a particle size from about 100 microns to about 500 microns, more preferably, from about 100 to about 300 microns, from about 150 to about 350 microns, from about 200 to about 350 microns, and even more preferably, the particle size is from about 100 to about 200 microns, from about 150 to about 250 microns, from about 200 to about 300 microns, from about 200 to about 400 microns, from about 250 to about 350 microns, from about 250 to about 450 microns, from about 300 to about 400 microns, from about 300 to about 500 microns, from about 350 to about 450 microns, and/or from about 400 to about 500 microns in size. It has been found that particle sizes within these ranges are coatable and provide ease of swallowing without urging the user to bite down. For example, it has been found that in preferred embodiments, a particle size of from about 250 to about 350 microns balances the ability to coat with the ability to avoid the gritty "mouth feel". The particle size can be determined by laser light scattering for instance using a Malvern Mastersizer Apparatus MS 2000 equipped with a Hydro S dispersion unit. Micronization of compounds of Formula I, for example, may be performed in the dry state using dry mills such as cutting mills, pin/cage mills, hammer mills, jet mills, fluidized bed jet mills and ball mills.

A preferred excipient that may be used to prepare the granular core is a binder. The binder may be any water soluble pharmaceutically acceptable polymer. In one embodiment, the compound of Formula I (or a pharmaceutically acceptable salt, solvate or prodrug thereof) is in the form of a powder which the binder necessarily bonds together due to the poor cohesive properties of most powders. Preferably, the binder is selected from povidone (polyvinylpyrrolidone), copovidone (vinylpyrrolidone-vinylacetate copolymer), microcrystalline cellulose, powdered cellulose, crystalline cellulose, siliconized microcrystalline cellulose, cellulose derivatives such as hydroxymethylcellulose, hydroxyethylcellulose, hydroxypropylcellulose and hydroxypropylmethylcellulose, starch, pregelatinized starch, polymethacrylates, compressible sugars, sucrose and sugar alcohols such as mannitol, sorbitol, maltitol and xylitol and mixtures thereof. More preferably, the binder is hydroxypropyl cellulose (Klucel LF).

The granules used in the high loading liquid oral pharmaceutical composition are preferably prepared by direct spheronization involving preparing a granular core comprising from about 60 to about 97 weight percent of a compound of Formula I (or a pharmaceutically acceptable salt, solvate or prodrug thereof), preferably from about 75 to about 97 weight percent, and more preferably from about greater than 90 weight percent to 97 weight percent, and from about 3 to about 40 weight percent of a binder, preferably from about 3 to about 25 weight percent, and more preferably from about 3 to about 10 weight percent, wherein the weight percent is based on the total weight of the granular core. The granulation can be carried out under high shear (mixer granulation) or in a fluidized bed (fluidized bed granulation).

The granular cores are optionally seal coated with a water-soluble seal coating in an amount to provide from about 0.5 to about 5 percent weight gain, from about 0.5 to about 3 percent weight gain, from about 0.5 to about 2 percent weight gain, from about 0.5 to about 1 percent weight gain, from about 1 to about 2 percent weight gain, from about 1 to about 3 percent weight gain, from about 1 to about 4 percent weight gain, from about 2 to about 3 percent weight gain, from about 2 to about 4 percent weight gain, from 1 percent weight gain, from 2 percent weight gain, from 3 percent weight gain, or from 4 percent weight gain. It has been found that applying a water-soluble seal coating generates a smooth and uniform granule which is more receptive to receiving an enteric coating. Preferred water-soluble polymers include hydroxypropylmethylcellulose (HPMC), carboxymethylcellulose (sodium and calcium salts), ethylcellulose, methylcellulose, hydroxyethylcellulose, ethyl hydroxyethylcellulose, hydroxypropylcellulose (HPC), L-HPC (low-substituted HPC), polyvinylpyrrolidone, polyvinyl alcohol, polymers of acrylic acid and its salts, vinylpyrrolidone-vinyl acetate copolymers (for example Kollidon® VA64, BASF), gelatine, guar gum, partially hydrolysed starch, alginates and xanthan. Most preferably, the water-soluble polymer is hydroxypropylmethyl cellulose. The seal coating is preferably applied by means of a bottom spray fluidized bed coater equipped with a Wurster column.

In addition to the seal coating or in the absence of a seal coating, the granular cores may optionally be coated with an enteric coating directly on the granular core or on a seal coating previously applied to the granular cores. Preferably, the enteric coating is applied in an amount to provide from about 0.5 to about 50 percent weight gain, from about 1 to about 40 percent weight gain, from about 2 to about 30 percent weight gain, from about 3 to about 20 percent weight gain, or from about 4 to about 10 percent weight gain, based on the total weight of the granular core. More preferably, the enteric coating is applied in an amount to provide from about 0.5 to about 5 percent weight gain, from about 1 to about 4 percent weight gain, or from about 2 to about 3 percent weight gain, based on the total weight of the granular core. The enteric coating is preferably applied by means of a bottom spray fluidized bed coater equipped with a Wurster column.

The enteric coating comprises a polymer selected from an acrylate polymer or an aqueous cellulose dispersion. Combinations of acrylate polymers and/or aqueous cellulose dispersions may also be used. Preferably, the acrylate polymer is selected from polymethacrylate methylmethacrylate copolymer (Eudragit® L-100), polyethylacrylate methylmethacrylate trimethylammonioethyl methacrylate chloride copolymer (Eudragit RL-100, RS-100), polymethacrylate ethylacrylate copolymer (Eudragit® L30D-55), ethylacrylate methylmethacrylate trimethylammonioethyl methacrylate chloride copolymer (Eudragit® RL30D), ethylacrylate methylmethacrylate trimethylammonioethyl methacrylate chloride copolymer (Eudragit® RS30D), and polyethylacrylate methylmethacrylate copolymer (Eudragit® NE30D). More preferably, the acrylate polymer is polymethacrylate ethylacrylate copolymer (Eudragit® L30D-55). The enteric coating may be preferably applied by means of a bottom spray fluidized bed coater equipped with a Wurster column. The enteric coating may increase delivery of the active pharmaceutical ingredient to a region of the gastrointestinal tract of a subject in which the pH is between about 4.5 and about 6.5. The enteric coating also increases delivery of the compound of Formula I (or a pharmaceutically acceptable salt, solvate or prodrug thereof) to the proximal or mid-small intestine or both. In addition, the enteric coating may increase delivery of the compound of Formula I (or a pharmaceutically acceptable salt, solvate or prodrug thereof) to one or more of the duodenum, jejunum, or mid-ileum. Preferably, the enteric coating begins to dissolve in an aqueous solution at pH between about 4.5 to about 5.5.

The vehicle to enhance the stability of the high drug loading liquid oral pharmaceutical composition may preferably be a protective colloid.

The high loading liquid oral pharmaceutical composition of the invention may additionally contain a plasticizer. Preferred plasticizers are diethyl phthalate, dibutyl phthalate, triethyl citrate, and glycerol. A combination of plasticizers may also be used. More preferably, the plasticizer is triethyl citrate.

In one embodiment, the high loading liquid oral pharmaceutical composition is in the form of a solution. In another embodiment, the high loading liquid oral pharmaceutical composition is in the form of a suspension. To form a suspension, the enteric coated granules may be combined with a liquid suspension formulation. The liquid suspension formulation may comprise a suspending agent, a vehicle to enhance the stability of the high drug loading liquid oral pharmaceutical composition, and a diluent. The suspending agent and the vehicle to enhance the stability of the high drug loading liquid oral pharmaceutical composition may be the same or different since many suspending agents also serve as stability enhancers.

Examples of suspending agents include, but are not limited to, methylcellulose, sodium carboxymethylcellulose, hydroxyethylcellulose, hydroxypropylmethylcellulose, gum tragacanth, and glycerol monostearate. More preferably, the vehicle to enhance the stability of the liquid oral pharmaceutical composition is a protective colloid. Examples of protective colloids include, but are not limited to, hydroxymethylcellulose, carboxymethylcellulose sodium, polyvinylalcohol, gelatin, and polyvinyl pyrrolidone. A combination of protective colloids may also be used. A preferred protective colloid is a mixture of cellulose gum, xanthan gum, and carrageenan. Examples of diluents include, but are not limited to, water, alcohols (such as for example methyl alcohol, ethyl alcohol, propyl alcohol, i-propyl alcohol etc.), acetone, glycerin, oils (such as for example castor oil), any other pharmaceutically acceptable diluent or mixtures thereof. Most preferably, water is used as the suspension or solution diluent. In addition, a pH modifier and/or an antioxidant may also be used.

In some specific embodiments of a liquid suspension formulation of the invention, the formulation includes: microcrystalline cellulose and carboxymethylcellulose sodium (Avicel RC-591), gum (CP Kelco), and water; or microcrystalline cellulose and carboxymethylcellulose sodium (Avicel RC-591), cellulose gum, xanthan gum, and carrageenan (Ticaloid Ultrasmooth), and water.

In accordance with a preferred embodiment, the liquid suspension formulation includes from about 0.5% to about 3% of at least one suspending agent; from about 0.5% to about 1% of at least one protective colloid; and about 98% of a diluent, wherein the weight percent values are based on the weight of the liquid suspension formulation. More preferably, the protective colloid will be used in an amount of about 0.1 to 0.5 weight percent. In some specific embodiments, the liquid suspension formulation includes about 1.5% of at least one suspending agent; from about 0.2% of at least one protective colloid; and about 98% of a diluent.

Preferably, the high drug loading liquid oral pharmaceutical composition in suspension form has a viscosity less than about 5 Pa s. More preferably, high drug loading liquid oral pharmaceutical composition in suspension form has a viscosity less than about 3 Pa s, and most preferably, less than about 1 Pa s.

In some embodiments, the high drug loading liquid oral pharmaceutical composition is used to prevent and/or treat a lysosomal storage disease selected from: Gaucher's disease (including Type 1, Type 2 and Type 3 Gaucher's disease), Pompe disease (including infantile and late-onset forms) and Fabry disease, or to prevent and/or treat (e.g., alleviate the symptoms) of PD. See e.g., Lukas J. et al. "*Enzyme enhancers for the treatment of Fabry and Pompe disease*.' Mol Ther. 2015 March; 23(3):456-64.

In some more specific embodiments, the high drug loading liquid oral pharmaceutical composition is used to prevent and/or treat AD or other diseases associated with pathological protein misfolding, aggregation and deposition (including Parkinson's disease (PD), Huntington's disease (HD), Amyotrophic Lateral Sclerosis (ALS) (i.e., Lou Gehrig's Disease), Pick's Disease, Gaucher's Disease and Frontotemporal degeneration (FTD)). In some further specific embodiments, the high drug loading liquid oral pharmaceutical composition is used to prevent and/or treat a subject with a mutation in a glucocerebrosidase (GCase) (e.g., a mutation in a beta glucocerebrosidase, wherein the subject may also have either Gaucher's, AD and/or Parkinson's Disease). The mutation in beta glucocerebrosidase may be selected from:

a. A point mutation at any one of the following positions: D140H, V15L, G46E, K79N, R119Q, P122S, R131L, K157Q, N188S, Y212H, F2131, F216V, F216Y, H225Q, F251L, R257E, P289L, A309V, H311R, W312C, Y3231, G325R, E326K, C342G, R353G, R359X (termination), S364T, N370S, L371V, G377S, V394L, V398F, P401L, D409H, D409V, P415R, L444P, A456P, V460V, R463C, G478S, or R496H and/or any combination thereof;
b. A point mutation at L444P;
c. A point mutation at N370S;
d. A point mutation at E326K;
e. Point mutations at L444P, A456P, and V460V;
f. Point mutations at D140H and E326K;
g. Point mutations at H255Q and D409H;
h. A guanine insertion at 84GG;
i. A splice site mutation in intron 2 (IVS2DS+1G-A), resulting in the skipping of exon 2;
j. A 1-bp deletion (1023delC in the genomic sequence) in the GCase gene,
k. A55-bp deletion (nucleotides 5879-5933 in genomic DNA) in the GCase gene; 1. A homozygous 259C-T transition (1763 in the genomic DNA);
m. A homozygous 1-bp deletion in the GCase gene, resulting in a frameshift and premature truncation of the protein in exon 6; and
n. A G-to-A substitution at the first position in the splice site of intron 10 of the GCase gene, resulting in the insertion of the first 11 base pairs of IVS10 and deletion of the first 11 base pairs of exon 11.

In some embodiments, the high drug loading oral liquid pharmaceutical composition may be given to a subject who is also receiving enzyme replacement therapy (e.g., combination therapy). Examples of such enzyme replacement therapy include, but are not limited to recombinant glucocerebrosidase, such as, for example, Imiglucerase, Velaglucerase, Taliglucerase alfa (ELELYSO®), and/or Eliglustat (CERDELGA®). The high drug loading oral liquid pharmaceutical composition may be administered simultaneously, sequentially or at different times with the enzyme replacement therapy.

In some embodiments, the high drug loading oral liquid pharmaceutical composition comprises an analog of ambroxol or an analog of bromhexine according to Formula I, or a pharmaceutically acceptable salt thereof, for treating a subject having a misfolded and/or erroneously transported glucocerebrosidase. In further embodiments, the high drug loading oral liquid pharmaceutical composition comprises an analog of ambroxol or an analog of bromhexine according to Formula I, or a pharmaceutically acceptable salt thereof, for treating or preventing a lysosomal storage disorder in a subject. In yet further embodiments, the high drug loading oral liquid pharmaceutical composition comprises an analog of ambroxol or an analog of bromhexine according to Formula I, or a pharmaceutically acceptable salt thereof, for treating a subject having a mutation in a glucocerebrosidase. In yet still further embodiments, the high drug loading oral liquid pharmaceutical composition comprises an analog of ambroxol or an analog of bromhexine according to Formula I, or a pharmaceutically acceptable salt thereof, for treating a subject having a mutation in a beta-glucocerebrosidase. Also, in some preferred embodiments, the mutation in beta-glucocerebrosidase is selected from N370S, L444P, and/or E326K. In a further embodiment, the high drug loading oral liquid pharmaceutical composition comprises an analog of ambroxol or an analog of bromhexine according to Formula I, or a pharmaceutically acceptable salt thereof, for treating a subject suffering from Gaucher's disease. In a further embodiment, the high drug loading oral liquid pharmaceutical composition comprises an analog of ambroxol or an analog of bromhexine according to Formula I, or a pharmaceutically acceptable salt thereof, for treating a subject suffering from PD.

The pharmaceutical composition of the invention may also be formulated in a unit dosage form, each dosage containing from about 50 to about 1000 mg, more typically, about 250 to about 500 mg of the compound of Formula I per unit dosage. The term "unit dosage form" refers to physically discrete units suitable as a unitary dosage for human subjects and other mammals, each unit containing a predetermined quantity of the compound of Formula I calculated to produce the desired therapeutic effect, in association with a suitable pharmaceutically acceptable carrier.

In further preferred embodiments, the compound of Formula I (or a pharmaceutically acceptable salt, solvate or prodrug thereof) is administered as several doses over a given period of time, e.g., a daily dose for a week or more. For example, a daily dosage from about 20-500 mg/day, 50-150 mg/day, 50-200 mg/day, 50-250 mg/day, 250-500 mg/day, 250 mg-1000 mg/day, 1000-1500 mg/day, 1500-2000 mg/day, or 1000-2000 mg/day may be utilized. Higher or lower doses are also contemplated as it may be necessary to use dosages outside these ranges in some cases. The daily dosage may be divided, such as being divided equally into two to four times per day daily dosing.

The pharmaceutical composition of the invention may also be formulated to provide slow or controlled release of the active ingredient(s) therein using, for example, hydroxypropylmethylcellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents using a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566, describes the use of polymeric microparticles that release antiparasitic compositions. Any or all of these techniques may be adapted for the controlled-release of compounds of Formula I (or a pharmaceutically acceptable salt, solvate or prodrug thereof).

The controlled-release of the compound of Formula I (or a pharmaceutically acceptable salt, solvate or prodrug thereof) may also be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the compound of Formula I (or a pharmaceutically acceptable salt, solvate or prodrug thereof) in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a subject, preferably a human or other mammal, having a body temperature high enough to induce gel formation of the sol-gel matrix, thereby releasing the active ingredient into the subject.

Compositions comprising compounds of the invention that are suitable for administration intranasally or by inhalation are of particular interest. As such, the compound of Formula I may be formulated for administration intranasally or by inhalation, typically in the form of a dry powder (either alone, as a mixture, for example, in a dry blend with lactose in anhydrous or monohydrate form, preferably monohydrate, mannitol, dextran, glucose, maltose, sorbitol, xylitol, fructose, sucrose or trehalose, or as a mixed component particle, for example, mixed with phospholipids) from a dry powder inhaler or as an aerosol spray from a pressurized container, pump, spray, atomizer (preferably an atomizer using electrohydrodynamics to produce a fine mist), or nebulizer, with or without the use of a suitable propellant, such as dichlorofluoromethane.

The pressurized container, pump, spray, atomizer, or nebulizer contains a solution or suspension of the compound of Formula I (or a pharmaceutically acceptable salt, solvate or prodrug thereof) comprising, for example, ethanol (optionally, aqueous ethanol) or a suitable alternative agent for dispersing, solubilizing or extending release of the compound, the propellant(s) as solvent and an optional surfactant, such as sorbitan trioleate or an oligolactic acid.

Prior to use in a dry powder or suspension formulation, the compound of Formula I (or a pharmaceutically acceptable salt, solvate or prodrug thereof) is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

A suitable solution formulation of the compound of Formula I (or a pharmaceutically acceptable salt, solvate or prodrug thereof) for use in an atomizer using electrohydrodynamics to produce a fine mist, may contain from 1 μg to 20 mg of the compound per actuation and the actuation volume may vary from 1 μL to 100 μL A typical formulation may comprise the compound of Formula I, propylene glycol, sterile water, ethanol and sodium chloride. Alternative solvents which may be used instead of propylene glycol, include glycerol and polyethylene glycol. Capsules, blisters and cartridges (made, for example, from gelatin or HPMC) for use in an inhaler or insufflator may be formulated to contain a powder mix of the compound of Formula I (or a pharmaceutically acceptable salt, solvate or prodrug thereof), a suitable powder base such as lactose or starch and a performance modifier such as L-leucine, mannitol, or magnesium stearate.

Formulations for inhaled/intranasal administration of the compound of Formula I (or a pharmaceutically acceptable salt, solvate or prodrug thereof) may be formulated to be immediate and/or modified release. Modified release formulations include delayed-, sustained-, pulsed-, controlled dual-, targeted- and programmed-release formulations. Sustained or controlled-release can be obtained by using, for example, poly(D,L-lactic-co-glycolic acid).

Administration of Compounds of the Invention

In some preferred embodiments, the compounds of the invention are administered orally to a patient. However, the compounds may be administered by any route, including by rectal, pulmonary, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration.

The dosing interval may be once a week, twice a week, every-other-day, once per day, typically once, twice, three times or four times per day with the doses given at equal intervals throughout the day and night in order to maintain a constant presence of the drug. However, those skilled in the art will be aware that a treatment schedule can be optimized for any given subject, and that administration of the compound of Formula I (or a pharmaceutically acceptable salt, solvate or prodrug thereof) may occur less frequently than once per day. The treatment may be carried out for as long a period as necessary.

The specific dose of a compound of Formula I (or a pharmaceutically acceptable salt, solvate or prodrug thereof) required to elicit a therapeutically beneficial response in the subject will, of course, be determined by the particular circumstances of the individual subject including the size, weight, age and sex of the subject, and the route of administration of the compound.

For example, a daily dosage from about 20-500 mg/day, 50-150 mg/day, 50-200 mg/day, 50-250 mg/day, 250-500 mg/day, 250-1000 mg/day, 1000-1500 mg/day, or 1000-2000 mg/day may be utilized. However, higher or lower doses are also contemplated as it may be necessary to use dosages outside these ranges in some cases. The daily dosage may be divided, such as being divided equally into two to four times per day daily dosing. Moreover, for long-term administration, as might be required in a method of inducing increasing and/or improving healthspan, lifespan, and/or mental acuity of a subject, the compound may, preferably, be administered at a dose of approximately 50 mg/day, 75 mg/day, 100 mg/day, 150 mg/day, 200 mg/day 250 mg/day, 300 mg/day, 350 mg/day, 400 mg/day, 450 mg/day, 500 mg/day, 550 mg/day, 600 mg/day, 650 mg/day, 700 mg/day, 750 mg/day, 800 mg/day, 850 mg/day, 900 mg/day, 950 mg/day, 1000 mg/day, 1050 mg/day, 1100 mg/day, 1150 mg/day, 1200 mg/day, 1250 mg/day, 1300 mg/day, 1350 mg/day, or between 50-150 mg/day, 50-200 mg/day, 50-250 mg/day, 250-500 mg/day, 250-1000 mg/day, or 1000-1500 mg/day or less than 1000 mg/day, or approximately 1 mg/kg/day, 2 mg/kg/day, 3 mg/kg/day, 4 mg/kg/day, 5 mg/kg/day, 6 mg/kg/day, 7 mg/kg/day, 8 mg/kg/day, 9 mg/kg/day, 10 mg/kg/day, 11 mg/kg/day, 12 mg/kg/day, and/or between 4-12 mg/kg/day.

The invention also provides a pharmaceutical pack or kit comprising one or more containers filled with one or more of the ingredients of the pharmaceutical composition of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

Without further description, it is believed that those skilled in the art can, using the preceding description and the following illustrative examples, readily make and utilize the compounds of Formula I (for example, the compounds shown in FIG. 1) or a pharmaceutically acceptable salt, solvate or prodrug thereof, and practice methods of the invention. The following examples point out some of the preferred embodiments of the present invention, but is not to be construed as limiting the disclosure in any way. Further, although the invention herein has been described with reference to embodiments, it is to be understood that such embodiments, and examples provided herein, are merely illustrative of the principles and applications of the present invention. It is therefore to be understood that numerous modifications can be made to the illustrative embodiments and examples, and that other arrangements can be devised without departing from the spirit and scope of the present invention as defined by, for example, the claims hereinafter. All patent applications, patents, literature and references cited herein are hereby incorporated by reference in their entirety.

EXAMPLES

The invention will now be further illustrated with reference to the following examples. It will be appreciated that what follows is by way of example only and that modifications to detail may be made while still falling within the scope of the invention.

Example 1: Synthesis of ZW-010

Compounds shown in FIG. 1 may be synthesized by adapting one or more synthetic scheme described in Latli B et al., J Label Compd Radiopharm 53:15-23, 2010 and/or the synthetic methods shown below for the synthesis of the difluoro- and dimethoxy-analogs of ambroxol, ZW-010 and ZW-011, respectively, and/or any other method known to those skilled in the art.

Synthesis of Compound ZW-010

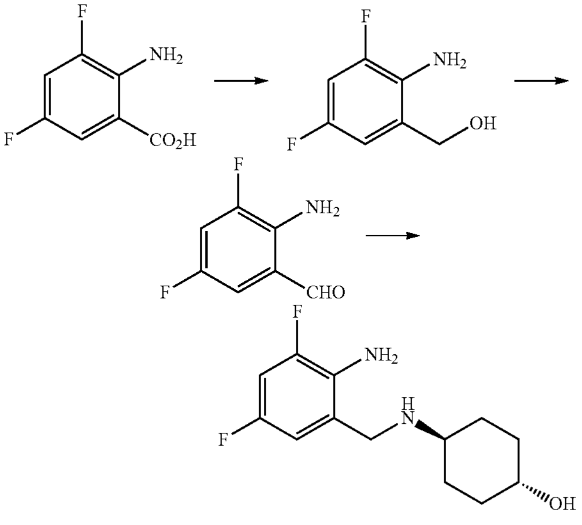

1. Synthesis of (2-amino-3.5-difluorophenyl)methanol

A cooled (0° C.) solution of 2-amino-3,5-difluoro-benzoic acid (500 mg, 2.89 mmol) in anhydrous tetrahydrofuran (THF, 15 ml) under nitrogen was treated dropwise with a 2.4 M lithium aluminum hydride solution in THF (2.54 ml, 6.11 mmol). After the addition was complete, the reaction mixture was stirred at ambient temperature for 1 hour, then cooled to 0° C. and quenched with 2.0 N aqueous sodium hydroxide (NaOH). The aqueous mixture was filtered through celite and the filtrate was extracted with 2×50 mL portions of dichloromethane. The combined organic extracts were dried ($Na_2SO_4$), filtered, and concentrated to an orange, crystalline solid which was used without further purification (302 mg, 66%). MS (APCI): m/z 160.

2. Synthesis of 2-Amino-3.5-Difluorobenzaldehyde

A solution of (2-amino-3,5-difluorophenyl)methanol (302 mg, 1.90 mmol) in toluene (15 mL) was treated with manganese (IV) oxide (1.50 g, 15.20 mmol, 88%) and the reaction mixture was stirred at 80° C. for 30 minutes. After cooling to ambient temperature, the excess reagent was filtered off (using a celite pad) and the filtrate was concentrated. Elution through a small plug of flash silica gel (silica gel 60, 230-400 mesh, 7:3 v/v hexanes:ethyl acetate (EtOAc)) gave the product as a yellow oil which crystallized on standing (143 mg, 48%). MS (APCI): m/z 158.

3. Synthesis of trans-{4-[(2-amino-3.5-difluorophenyl)methyl]amino}cyclohexanol. ZW-010, as the Hydrochloride Salt A mixture of 2-amino-3,5-difluorobenzaldehyde (140 mg, 0.89 mmol) and trans-4-aminocyclohexanol (103 mg, 0.891 mmol) in ethanol (15 mL) was heated at 80° C. for 5 hours then allowed to cool to ambient temperature. Sodium borohydride (81 mg, 2.14 mmol) was then added and stirring at ambient temperature was continued for 2 hours before quenching with a saturated ammonium chloride ($NH_4Cl$) solution in water. The mixture was basified by addition of a saturated sodium bicarbonate solution and the product was extracted with EtOAc. The organic extract was dried ($Na_2SO_4$), filtered, and concentrated. Elution through a flash chromatography column (silica gel 60, 230-400 mesh, 1:9 v/v methanol:EtOAc) gave a clear oil with the correct mass [MS (APCI): m/z 257]. The free base was taken up in EtOAc and the solution was treated dropwise with a 5-6 N HCl solution in isopropanol to precipitate the hydrochloride salt as an off-white solid. The precipitate was filtered, washed with EtOAc, and dried in vacuo at 35° C. to give the pure hydrochloride salt of ZW-010 (180 mg, 69%). MS (ESI): m/z 257.1 $(M+H)^+$; 1H NMR (MeOD-d4) δ (ppm): 1.35 (m, 2H), 1.60 (m, 2H), 2.1 (m, 2H), 2.25 (m, 2H), 3.25 (m, 1H), 3.6 (m, 1H), 4.3 (s, 2H), 7.1 (m, 2H)

Example 2: Synthesis of Compound ZW-011

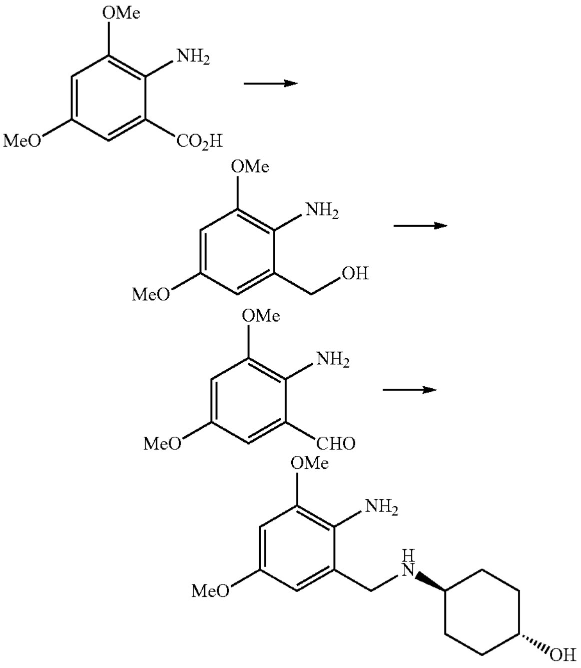

1. Synthesis of (2-amino-3.5-dimethoxy)methanol

A cooled (0° C.) solution of 2-amino-3,5-dimethoxybenzoic acid (1.0 g, 5.07 mmol) in anhydrous THF (30 mL) under nitrogen was treated dropwise with a 2.4 M lithium aluminum hydride solution in THF (4.44 mL, 10.65 mmol). After the addition was complete, the reaction mixture was stirred at ambient temperature for 1 hour, re-cooled to 0° C. and quenched with 2.0 N NaOH. The aqueous mixture was filtered through celite and the filtrate was extracted with 2×50 mL portions of dichloromethane. The combined organic extracts were dried ($Na_2SO_4$), filtered, and concentrated. Elution through a flash column (silica gel 60, 230-400 mesh, 7% MeOH in EtOAc) gave the product as an orange crystalline solid (870 mg, 94%). MS (APCI): m/z 184.

2. Synthesis of 2-amino-3.5-dimethoxybenzaldehyde

A solution of (2-amino-3,5-dimethoxy)methanol (870 mg, 4.75 mmol) in dichloromethane (40 mL) was treated with manganese (IV) oxide (3.75 g, 38.00 mmol, 88%) and the reaction mixture was stirred at ambient temperature for 1.5 hours. The excess reagent was then filtered off (celite pad) and the filtrate was concentrated. Elution through a flash column (silica gel 60, 230-400 mesh, 1:1 v/v hexanes: EtOAc) gave 2-amino-3,5-dimethoxybenzaldehyde as a yellow oil (270 mg, 31%). MS (APCI): m/z 182.

3. Synthesis of trans-4-{[(2-amino-3.5-dimethoxyphenyl)methyl]amino}cyclohexanol, ZW-011 as the Hydrochloride Salt A mixture of 2-amino-3,5-dimethoxybenzaldehyde (270 mg, 1.49 mmol) and trans-4-aminocyclohexanol (172 mg, 1.49 mmol) in ethanol (25 mL) was heated at 80° C. for 4 hours then allowed to cool to ambient temperature. Sodium borohydride (135 mg, 3.58 mmol) was then added and stirring at ambient temperature was continued for 1 hour before quenching with a saturated aqueous solution of ammonium chloride ($NH_4Cl$). The mixture was basified with a saturated aqueous solution of $NaHCO_3$ and extracted with ethyl acetate. The organic extract was dried ($Na_2SO_4$), filtered, and concentrated. Elution through a flash column (silica gel 60, 230-400 mesh, 45% MeOH in EtOAc) gave an orange oil (MS (APCI): m/z 281). The free base was taken up in EtOAc and the solution was treated dropwise with a 5-6 N HCl solution in isopropanol to precipitate the hydrochloride salt of ZW-011 as a light green, amorphous solid which was filtered, washed, and dried in vacuo at 35° C. (207 mg, 44%). MS (ESI): m/z 281.0 $(M+H)^+$; 1H NMR (MeOD-d4) δ (ppm): 1.35 (m, 2H), 1.60 (m, 2H), 2.1 (m, 2H), 2.25 (m, 2H), 3.3 (m, 1H), 3.6 (m, 1H), 3.9 (s, 3H), 4.0 (s, 3H), 4.3 (s, 2H), 6.8 (s, 2H)

Example 3: Metabolic Stability of Ambroxol Analogs

The metabolic stability of ambroxol and analogs was studied in the presence of human liver microsomes.

Study design—Test compounds (ambroxol and analogs) were dissolved in dimethylsulfoxide (DMSO) to prepare 1 mM stock solutions. The compounds were added to preparations of human liver microsomes (200 μL per incubation at a 1 mg/mL protein concentration) such that the final compound concentration was 1 μM. The samples were incubated at 37° C. in the presence of a reduced nicotinamide adenine dinucleotide phosphate (NADPH)-regenerating system (NADP, 1 mM, pH 7.4; glucose-6-phosphate, 5 mM, pH 7.4; glucose-6-phosphate dehydrogenase, 1 unit/mL). A positive control (midazolam, 1 μM, 0.1 mg/mL protein) was incubated concurrently to ensure the microsome preparation was performing as expected. Samples were obtained at t=0, 30, 60, and 120 min and quenched by addition of acetonitrile.

Quenched samples were analyzed by liquid chromatography coupled to tandem mass spectrometry detection (LC/MS-MS). The concentration of the test compounds at each time point were converted to percent remaining relative to the concentration of the compound at time t=0 (which serves as the 100% value). All data points were included in data processing. The rate constant of elimination ($k_{el}$, $min^{-1}$) of each test compound was determined from the time course of disappearance of the parent compound based on fitting the experimental data to a single exponential decay formula ($A_t=A_o e^{-k_{el}t}$, where $A_t$ is the % remaining at time t, $A_o$ is 100%, ka is the elimination rate constant, and t is time). The in vitro half-life ($t_{1/2}$) was determined from $k_{el}$ based on the formula: $t_{1/2}=\ln(2)/k_{el}$. The rate constant of elimination was also used to calculate the in vitro intrinsic clearance $CL_{int-microsomes}$ (μL/min/mg protein).

Results—Estimated in vitro elimination half-lives ($t_{1/2}$) and intrinsic clearances ($CL_{int-microsomes}$) for compounds ZW-010 and ZW-011 are presented in Table 2 where they are compared to the values obtained for parent compound ambroxol.

TABLE 2

In vitro elimination half-lives ($t_{1/2}$) and intrinsic clearances ($CL_{int-microsomes}$) for compounds studied

| | $t_{1/2}$ (min) | $CL_{int-microsomes}$ (μL/min/mg protein) |
|---|---|---|
| ZW-010 | >120 | <5.775 |
| ZW-011 | >120 | <5.775 |
| ambroxol | 60.8 | 11.4 |

At t = 120 min in presence of cofactors, there was 62.2% ZW-010 and 66.8% ZW-011 left.

As shown in Table 2, replacement of the 2 bromine substituents of ambroxol as in ZW-010 (two fluorine) and ZW-011 (two methoxy) leads to improved stability against metabolism as the elimination half-life of both compounds is increased by more than two-fold vs. ambroxol. This improved stability is unexpected. The increased stability of the analogs may allow for a higher exposure of the analog when administered. Additionally, the improved stability of the analog may also allow for a reduced dosing schedule as compared to ambroxol alone. Taken together, these improvements could lead to an improvement in the overall cost of goods of the analogs by decreasing, compared to ambroxol, the required dose level and dose frequency to achieve sustained efficacy.

Example 4: Comparative Pharmacokinetics (PK) of Ambroxol and ZW-010

After being acclimated to the study room for a minimum of 3 days, female C57BL/6 mice (6-8 weeks of age, 16-30 g, N=21 per group) were orally administered a single dose of ambroxol or ZW-010, as their hydrochloride salts, by gavage. Both compounds were dosed at 10 mg/kg (free base equivalent) as 1 mg/mL clear solutions in 5:95 v/v dimethylsulfoxide (DMSO)/saline. Volumes administered were calculated for each animal based on their most recent weight. Animals were fasted overnight prior to drug administration and food and water were returned 4 h after dose administration. Mice (N=3 per group) were sacrificed at 0.15, 0.25, 1, 2, 4, 8, and 24 h post-dose. Blood (K2EDTA collection tubes) and brain were collected from each animal at each time point. Plasma (isolated from blood samples by centrifugation) and brain homogenates (obtained by homogenization with 50% methanol in water in a 1:2 w/v ratio) were used to prepare samples for quantitative analysis (internal standard: verapamil) by HPLC/MS-MS (C18 column, gradient elution; standard curves from 1 to 3,000 ng/mL; electrospray, positive ionization mode, multiple reaction monitoring—MRM—mode). Concentrations (in ng/mL for plasma and in ng/g for brain) were calculated and a plot of the averages and standard deviations in plasma and brain as a function of time post-injection are presented in FIG. 2A (Ambroxol) and 2B (ZW-010).

As shown in FIGS. 2A and 2B, both compounds are brain-penetrant with a brain/plasma ratio >1 at all time points. It can also be observed that exposure to ZW-010 is significantly larger in both plasma and brain than exposure to ambroxol while both compounds were administered at the same dose (10 mg/kg). These results demonstrate that the halogen analogs of ambroxol have improved stability in the body, improving exposure in both the brain and periphery. These properties make the novel compounds ideal for treatment of disorders with both neurological and peripheral involvement described herein.

TABLE 3

Brain and Plasma PK Parameters in Female C57BL/6 Mice Administered a Single 10 mg/kg (free base equivalent) Oral Dose of Ambroxol or ZW-010 (as HCl Salts).

| | Parameter | Plasma | Brain | Brain/Plasma |
|---|---|---|---|---|
| Ambroxol | $T_{max}$ (h) | 0.15 | 0.15 | — |
| | $C_{max}$ (ng/ml, ng/g)* | 310 | 2940 | 9.5 |
| | $t_{1/2}$ (h) | 1.16 | 1.40 | — |
| | $AUC_{last}$ (ng · h/mL, ng · h/g)** | 421 | 4633 | 11.0 |
| ZW-010 | $T_{max}$ (h) | 0.25 | 0.25 | — |
| | $C_{max}$ (ng/ml, ng/g)* | 1900 | 5940 | 3.1 |
| | t1/2 (h) | 2.22 | 3.03 | — |
| | $AUC_{last}$ (ng · h/mL, ng · h/g)** | 2991 | 10774 | 3.6 |

*ng/ml for plasma, ng/g for brain

**ng · h/mL for plasma, ng · h/g for brain

As shown in Table 3, brain and plasma exposures to ZW-010 are higher than those to ambroxol. Both compounds are brain penetrant, and the brain/plasma ratio is >1.0 with a larger ratio for ambroxol (11.0) than for ZW-010 (3.6) although the absolute brain exposure (in ng·h/g) to ZW-010 is higher than to ambroxol. It should be noted that molar exposure to ZW-010 is even higher (AUClast=42.0 vs. 12.3 µM·h for ZW-010 and ambroxol, respectively). Additionally, the elimination half-life (t½) of ZW-010 is about 2-fold longer than that of ambroxol.

Thus, the improved metabolic stability of ZW-010 vs. ambroxol (see Example 3) leads to improved pharmacokinetics of ZW-010 compared to ambroxol with a significantly higher exposure in brain tissue when administered at the same dose and a significantly longer elimination half-life. These results suggest the potential of the compounds of the invention to allow for achieving efficacy at significantly lower doses than required for ambroxol and with a better dosing schedule (once or twice daily) thereby limiting the risks of off-target side-effects and potentially improving the cost of goods in the manufacture of the compounds.

Collectively, these data show that this novel ambroxol analog is expected to require lower, less frequent dosing than the parent compound. This is important given that high dose regime clinical trials of ambroxol have been prone to dropout due to low compliance of participants. See, Istaiti, M. et al., "High-Dose Ambroxol Therapy in Type 1 Gaucher Disease Focusing on Patients with Poor Response to Enzyme Replacement Therapy or Substrate Reduction Therapy," Int. J. Mol. Sci. 2023, 24, 6732 and NCT02941822.

Example 5: Biological Activity of Tested Compounds

Figure 3:
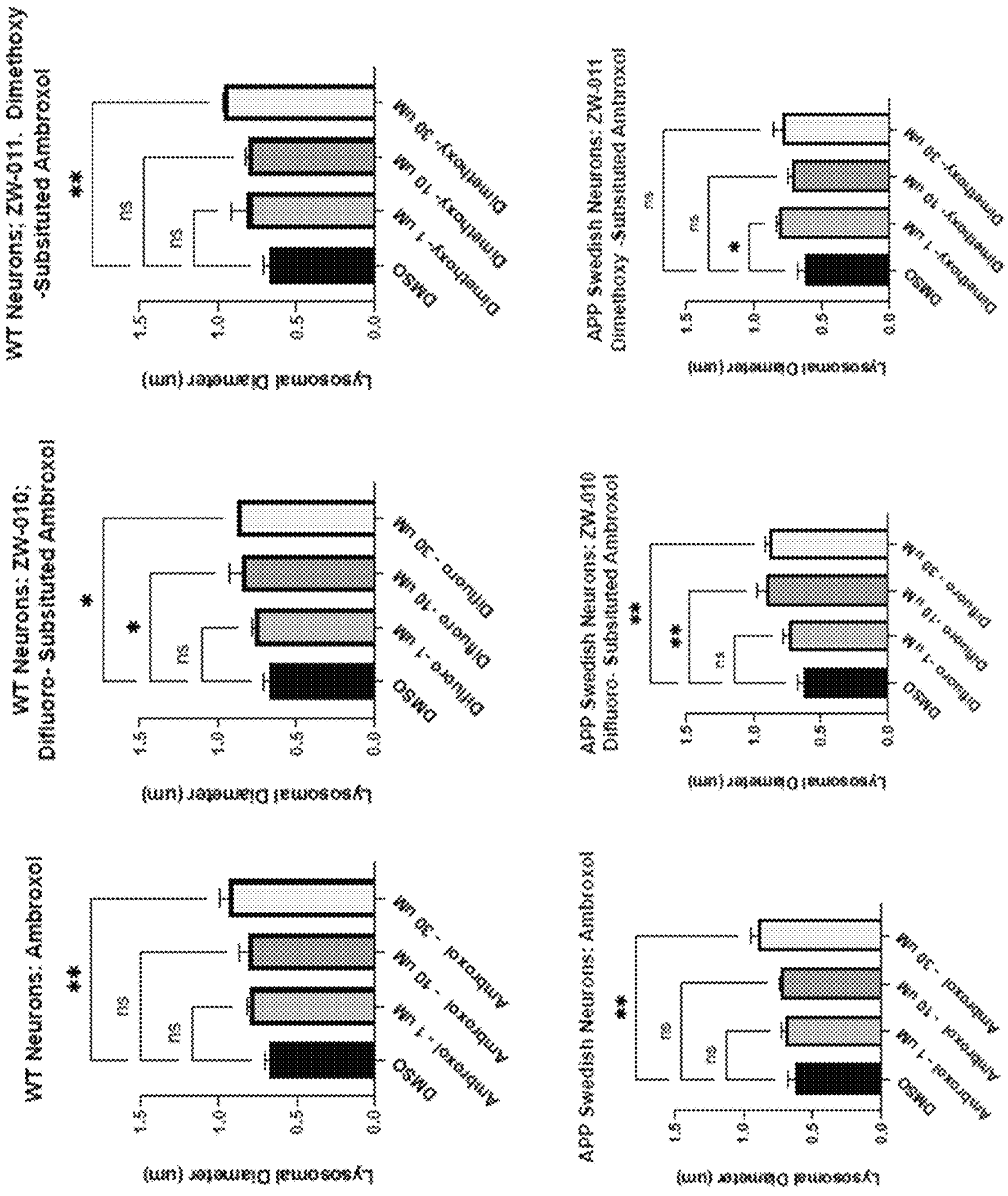
FIG. 3 shows that difluoro-substituted ambroxol (Compound 1; also referred to herein as "ZW-010") and dimethoxy-substituted ambroxol (Compound 5; also referred to herein as "ZW-011") both increase lysosomal size. To obtain the data, human induced pluripotent stem cell (iPSC)-derived neurons were grown in in culture for 14 days. Lysosomes were stained with "Lysotracker" and cells were fixed and imaged using confocal micrsosopy. Lysosomal size was measured using IMARIS software (Bitplane).

In FIG. 3 human neuronal inducible Pluripotent Stem Cells (iPSCs) were obtained from the New York Stem Cell Foundation. Cultured cells were differentiated and maintained in proprietary media from Stem Cell Technology. Compounds including ambroxol, difluoro-substituted ambroxol (Compound 1; also referred to herein as "ZW-010") and dimethoxy-substituted ambroxol (Compound 5; also referred to herein as "ZW-on") were dissolved in DMSO. Cells were treated for 14 days. Lysosomes were stained with "Lysotracker Green" (Invitrogen) following manufacturer's directions. Cells were fixed and 3D image stacks were acquired using a Leica SP8 laser scanning confocal microscope. Lysosomal size was quantitated using IMARIS 7.7 software (Bitplane). Human neurons were obtained from (Kwart D, Gregg A, Scheckel C, Murphy E A, Paquet D, Duffield M, Fak J, Olsen O, Darnell R B, Tessier-Lavigne M: A Large Panel of Isogenic APP and PSEN1 Mutant Human iPSC Neurons Reveals Shared Endosomal Abnormalities Mediated by APP beta-CTFs, Not Abeta. Neuron 2019, 104:256-270 e255. 31416668).

Figure 4:
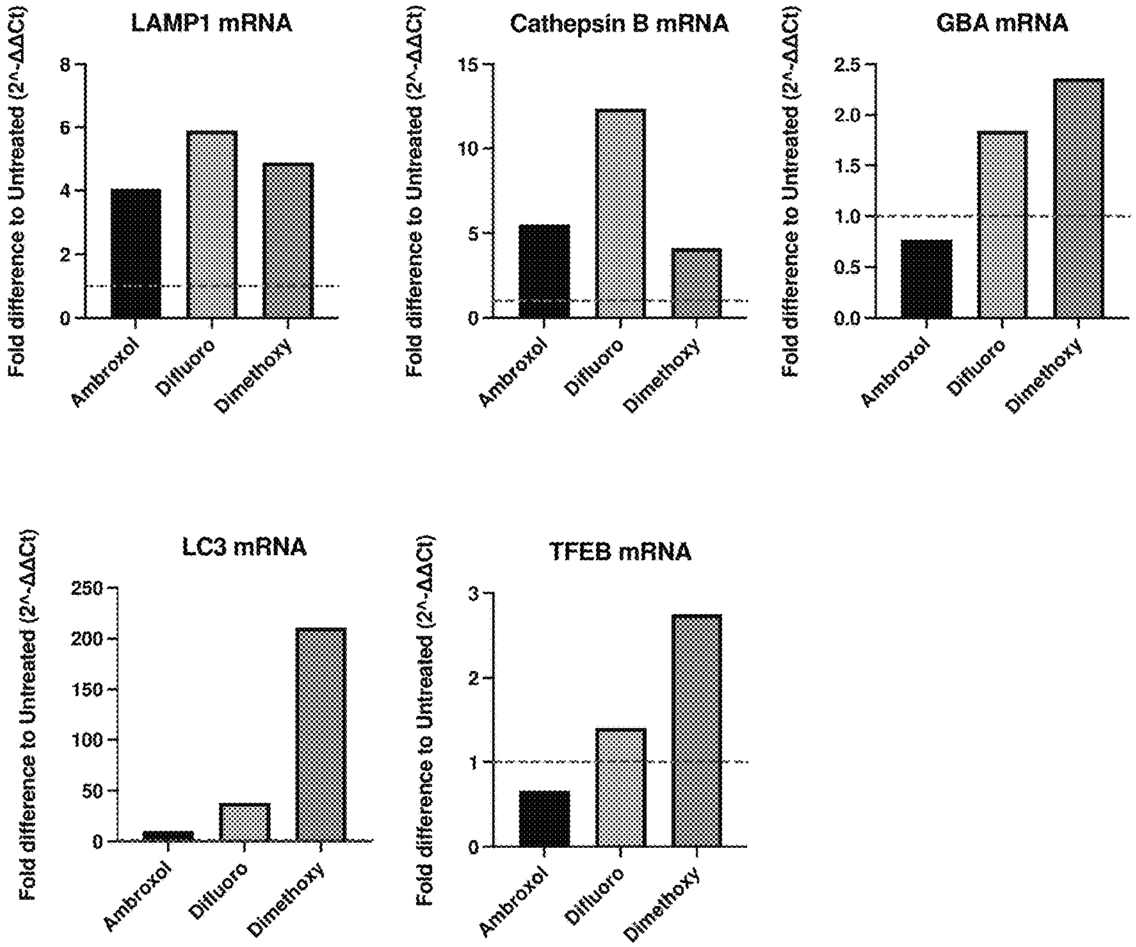
FIG. 4 shows that difluoro-substituted ambroxol (Compound 1; also referred to herein as "ZW-010") and dimethoxy-substituted ambroxol (Compound 5; also referred to herein as "ZW-011") both drive lysosomal and autophagosomal and TFEB gene expression. To obtain the data, N2A neuroblastoma cells were treated for 3 days with solvent alone (DMSO), ZW-010 (difluoro) or ZW-011 (dimethoxy) at 10 micromolar. Cells were extracted and mRNAs were quantitated by qPCR.

In FIG. 4, N2a Neuroblastoma cells were obtained from the American Tissue Type Collection (ATCC). Cells were plated in a 6-well plate at a density of 100,000 cells/well. Cells were given 24 hours in MEM supplemented with 10% Fetal Bovine Serum (FBS) and then differentiated by serum starvation in MEM for 24 hours. Cells were then treated with DMSO, ambroxol or difluoro-substituted ambroxol (Compound 1; also referred to herein as "ZW-010") and dimethoxy-substituted ambroxol (Compound 5; also referred to herein as "ZW-011") in MEM supplemented with 10% FBS. Cells were left in treated media for 24 hours then RNA was TRIzol-chloroform extracted. cDNA was created using an iScript cDNA synthesis kit (Bio-Rad), and RT-PCR was run using a SsoAdvanced Universal SYBR Green Supermix kit (Bio-Rad). The difluoro and dimethoxy compounds increased transcription of lysosome-associated LAMP1, Cathepsin B, GBA1, and autophagy-associated LC3 and TFEB to a greater extent than ambroxol.

Figure 5:
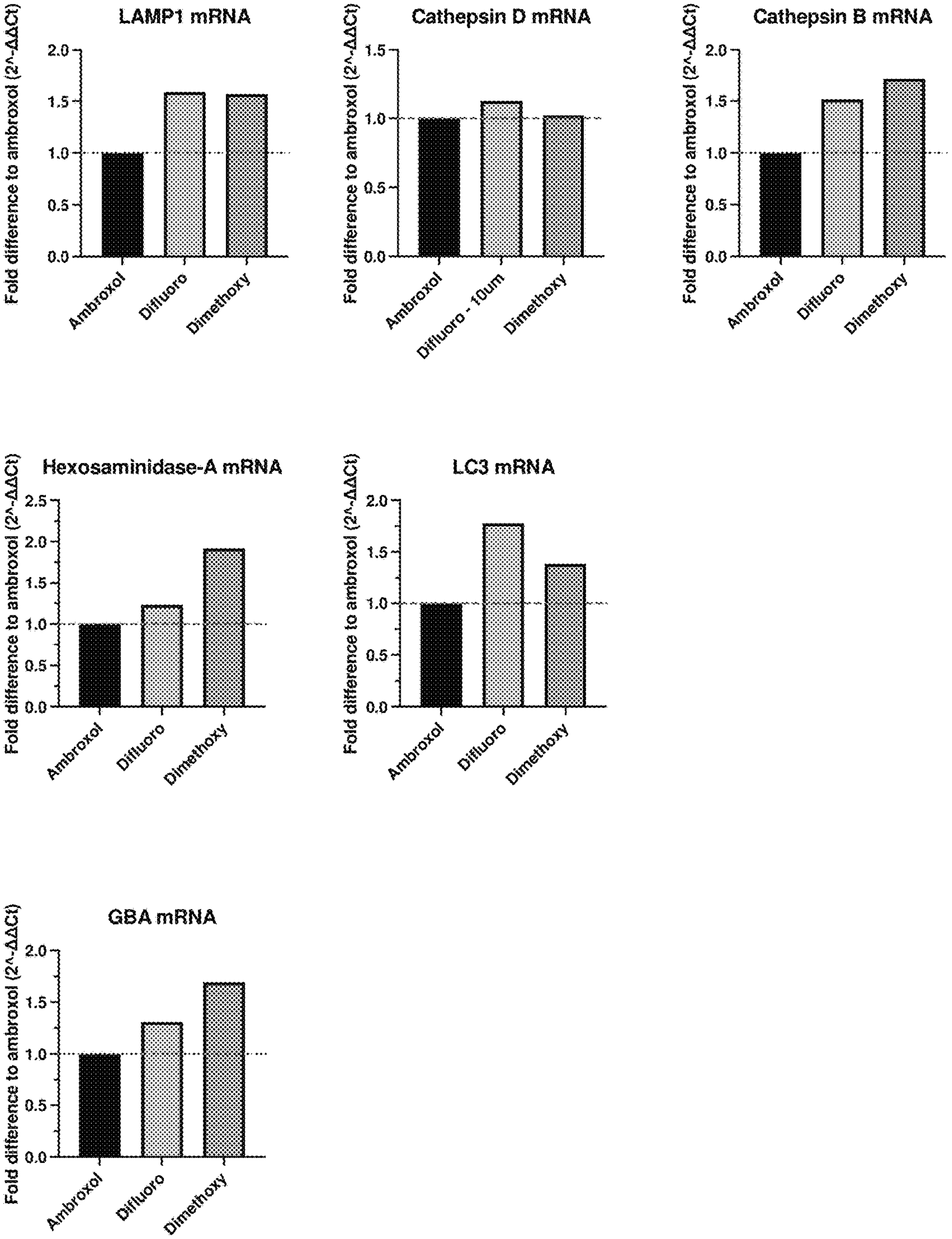
FIG. 5 shows that difluoro-substituted ambroxol (Compound 1; also referred to herein as "ZW-010") and dimethoxy-substituted ambroxol (Compound 5; also referred to herein as "ZW-011") both drive lysosomal and autophagosomal gene expression to a greater degree in iPSC-derived human neurons compared with ambroxol. To obtain the data, iPSC-derived human Neurons were treated for 3 days with solvent alone (DMSO), ZW-010 (difluoro) or ZW-011 (dimethoxy) at 10 micromolar. Cells were extracted and mRNAs were quantitated by qPCR.

In FIG. 5, Human iPSC-derived neurons (as in FIG. 3) were plated on two 6-well plates at a density of 150,000 cells/well. At 6 DIV, one 6-well plate was treated with equivalent DMSO (vehicle control) and another 6-well was treated with 10 mM [micromolar] of ambroxol or difluoro-substituted ambroxol (Compound 1; also referred to herein as "ZW-010") and dimethoxy-substituted ambroxol (Compound 5; also referred to herein as "ZW-011") at the first 50/50 media change. Cells were treated for 3 days and cells were TRIzol-chloroform extracted. cDNA was created using an iScript cDNA synthesis kit (Bio-Rad), and RT-PCR was run using a SsoAdvanced Universal SYBR Green Supermix kit (Bio-Rad). The difluoro and dimethoxy compounds increased transcription of lysosome-associated LAMP1, Cathepsin D, Cathepsin B, GBA1, and autophagy-associated LC3 and TFEB to a greater extent than ambroxol.

Figure 6:
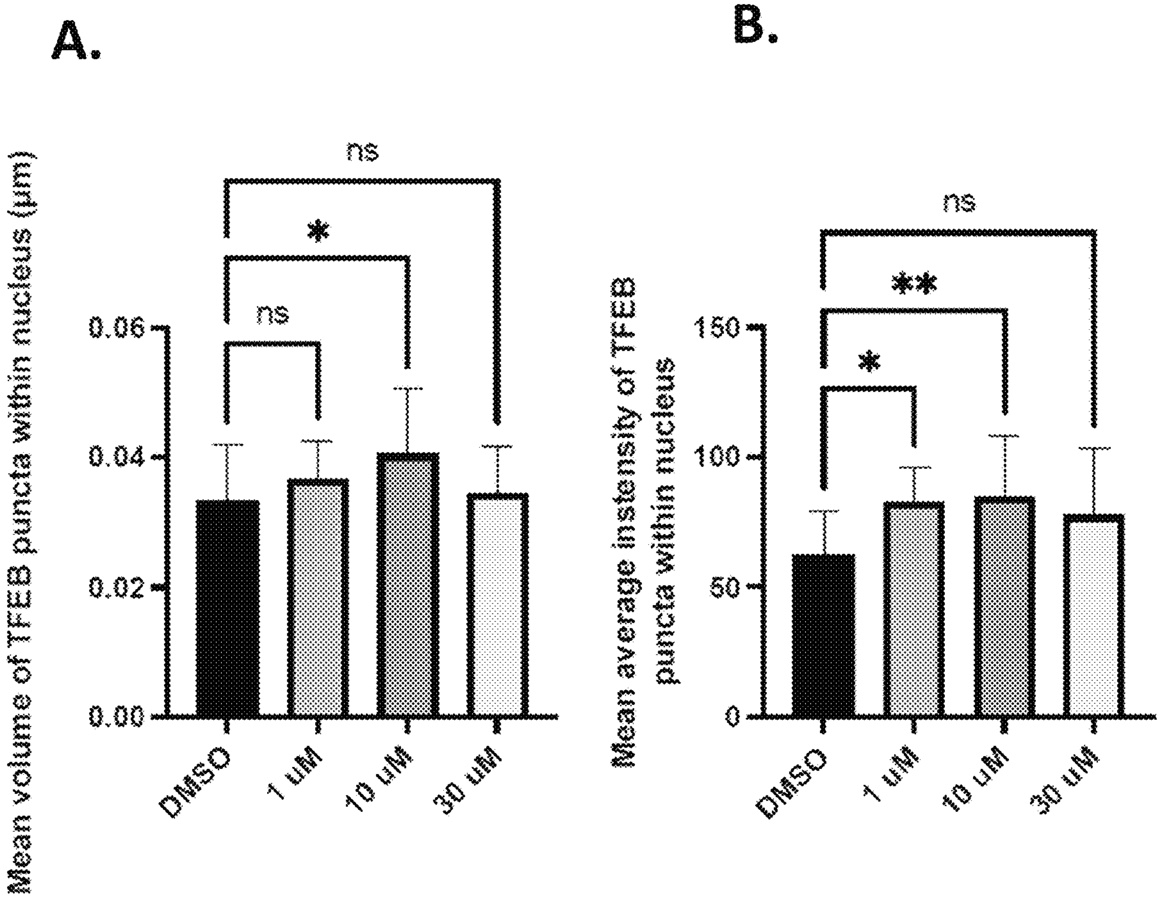
FIG. 6A-B shows that difluoro-substituted ambroxol (Compound 1; also referred to herein as "ZW-010") induces TFEB transfer to the nucleus (FIG. 6A). To obtain the data, human iPSC-derived neurons were treated with difluor-substituted-ambroxol for 14 days. Cells were fixed and endogenous TFEB was immunostained and nuclei were identified by DAPI staining. Cells were imaged on a Leica SP8 Confocal Microscope. TFEB signal appeared as puncta throughout the cytoplasm and nucleus (FIG. 6B). TFEB puncta within the nucleus were quantitated using IMARIS software (Bitplane).

FIG. 6A-B shows that difluoro-substituted ambroxol (Compound 1; also referred to herein as "ZW-010") induces TFEB transfer to the nucleus. Human iPSC-derived neurons were treated with difluoro-substituted-ambroxol for 14 days. Cells were fixed and endogenous TFEB was immunostained. Nuclei were identified by DAPI staining. Cells were imaged as 3D stacks on a Leica SP8 Confocal Microscope. TFEB signal appeared as puncta throughout the cytoplasm and nucleus (FIG. 6A). TFEB puncta within the nucleus were quantitated using IMARIS 7.7 software (Bitplane) (FIG. 6B).

Figure 7:
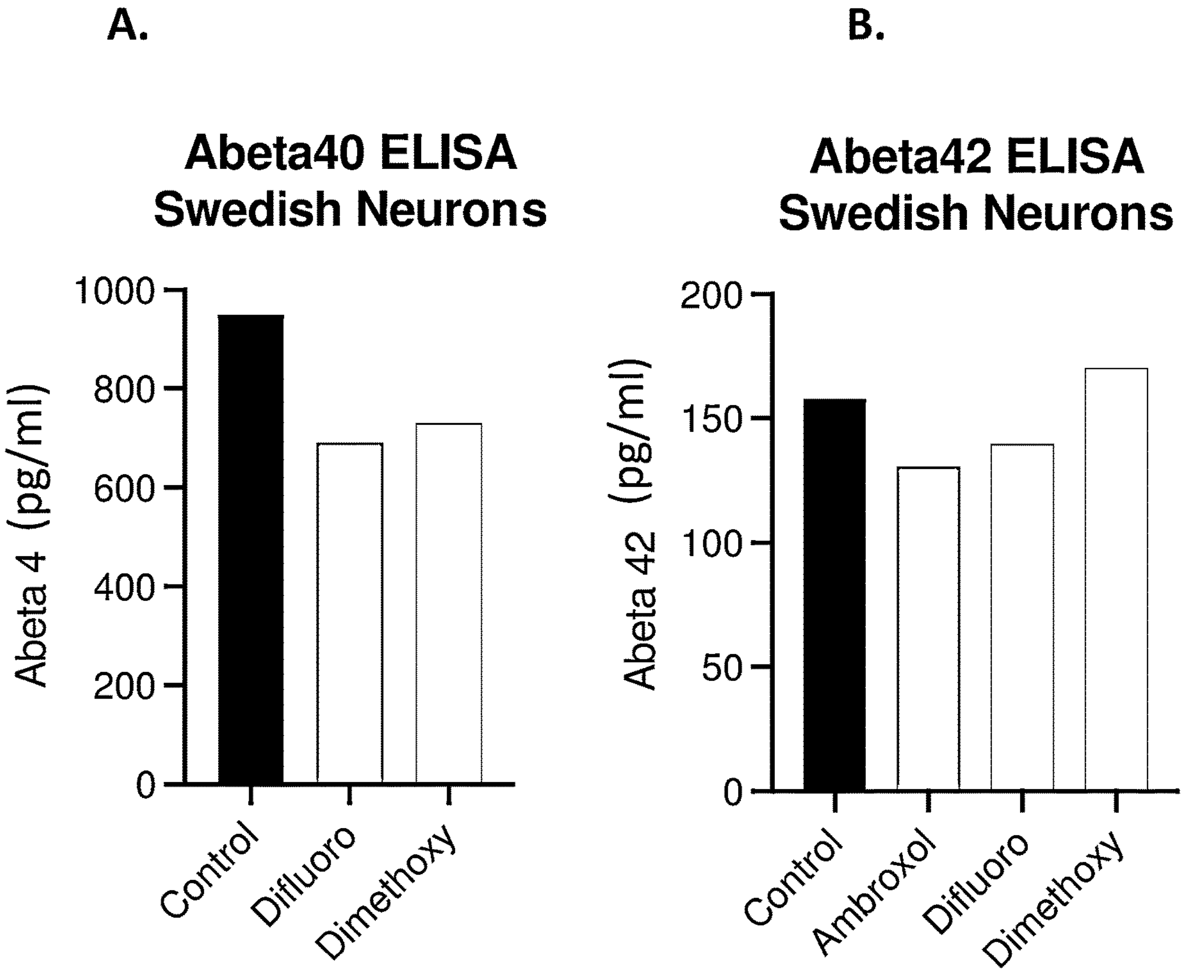
FIG. 7A-B shows that difluoro-substituted ambroxol (Compound 1; also referred to herein as "ZW-010") and dimethoxy-substituted ambroxol (Compound 5; also referred to herein as "ZW-011") decreased secretion of beta amyloid species Abeta40 (FIG. 7A) and Abeta42 (FIG. 7B) into the media of iPSC-derived human neurons bearing the Swedish amyloid precursor protein mutation. To obtain the data, iPSC-derived human neurons bearing the Swedish mutation were treated for 5 days with solvent alone (DMSO), Ambroxol ZW-010 (difluoro) or ambroxol ZW-011 (dimethoxy) at 10 micromolar. Media was collected and analysed by ELISA assay.

In FIG. 7A-B shows iPSC-derived human neurons bearing the Swedish mutation were differentiated and then maintained using media from Stem Cell Technologies. Cells were treated with DMSO (solvent), ambroxol, or difluoro-substituted ambroxol (Compound 1; also referred to herein as "ZW-010") for 5 days. Media was taken and analyzed by ELISA (Invitrogen) for Abeta 40 (FIG. 7A) and 42 (FIG. 7B)

following manufacturer's instructions. Ambroxol and its derivatives were both effective in reducing secretion of beta amyloid species.

Example 6: Compounds can be Shown to Improve Lifespan

Weaned male BDF1 mice raised from pups, housed 1-4 animals per cage and fed Teklad 7013 NIH-31 rodent chow and water ad libitum, at 2 months of age, are divided into two roughly equal groups of 22-25 animals. One group continues to be fed the Teklad chow as before (control); the other group is switched to Teklad chow formulated with any one of compounds 1-6 at 300 mg per kg of chow. This formulation was designed, based on the average ad libitum chow consumption of an adult male BDF1 mouse, to deliver 50 mg/kg/day (based on body mass) to each mouse in the treated group. Mice are maintained on this diet until they die naturally or until they reach 16 months of age, at which time the experiment ends. During the course of the experiment, all mice are periodically removed from their cages and handled in the course of subjecting them to various sensorimotor, cognitive, and/or behavioral tests.

Figure 8:
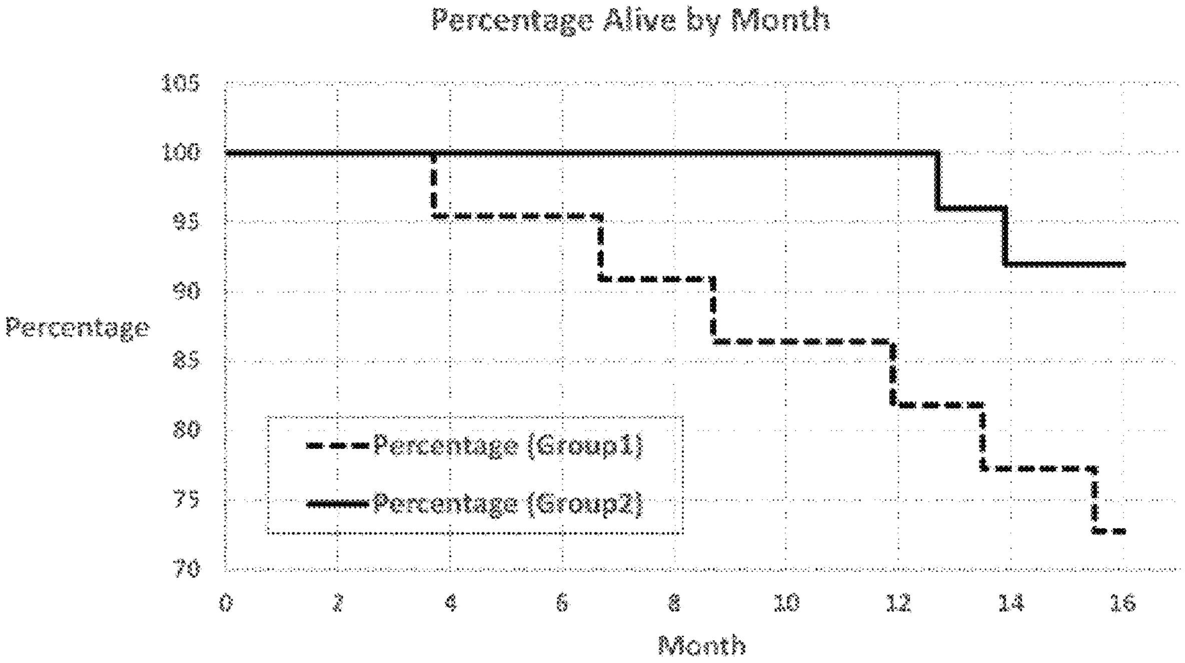
FIG. 8 provides animal data showing that ambroxol was able to increase lifespan in a mouse B6D2F1 model. Group 1 represents control animals that were not administered ambroxol; and Group 2 represents animals administered 50 mg/kg (body weight) of ambroxol daily as a chow supplement, starting at 2 months of age.

FIG. 8 provides animal data for an experiment as described in the preceding paragraph using ambroxol. It shows that ambroxol is able to increase lifespan in a mouse model. Group 1 represents control animals that were not administered ambroxol; Group 2 represents animals administered 50 mg/kg of ambroxol daily as a chow supplement, starting at 2 months of age. The data also suggests that not only did ambroxol increase lifespan, but that when sacrificed, surviving animals of Group 2 appeared to be at least as healthy, on average, as did the Group 1 animals, indicating that healthspan was extended in parallel with lifespan. It is anticipated that compounds 1 to 6 will achieve similar results.

Example 7: Studies with Compounds of the Invention Showing Activity in Improving Tremor in Mouse Model of PD Compounds of the present invention can be investigated for activity in improving tremor in a mouse animal model of Parkinson's Disease as follows.

6-OHDA mice (i.e., mice that have been injected with 6-hydroxydopamine into the striatum) showing rest tremor are selected. Three groups of mice, with at least 10 mice in each group, are administered with a "High Dose" (Group 1: 150 mg/kg/day of a compound of the present invention), "Low Dose" (Group 2: 50 mg/kg/day of a compound of the present invention), or no dosage of a compound of the present invention (Control Group); and tremor in the mice monitored daily using electromyography or force plate-based measurement (Bekar L et al., Nat Med 14:75-80, 2008) to assess the effect of a compound of the present invention on rest tremor.

Example 8: Studies with Compounds of the Invention Showing Effect on Aggregated A1 in Mouse Model of AD Compounds of the present invention can be investigated for activity on aggregated deposits of amyloid β peptide (Aβ) in a mouse animal model of Alzheimer's Disease as follows. FIG. 11 shows the results when ambroxol (FIG. 11B) versus control (FIG. 11A) were tested in the following mouse model. The analogs described herein can also be tested using this same model and are expected to show similar if not better results due to the improved pharmacokinetics and significantly higher exposure in brain tissue when administered at the same dose and a significantly longer in other models.

An AD mouse model showing significantly elevated production of Aβ3 is selected (e.g., a mouse including the "Swedish mutation" in the human amyloid precursor protein (APP)). Using two groups of the mice; that is, a "Treated" Group (2400 mg/kg introduction to animal feed of a compound of the present invention), and a Control Group (no a compound of the present invention), analysis can be made after appropriate periods of treatment (e.g., 2 months of treatment in animals of sufficient age to show substantial AD-related pathology) for the relative development of diffuse and fibrillar deposits of aggregated Aβ by, for example, comparing silver staining or Aβ immunohistochemistry against Congo red or thioflavin-S histology (Jankowsky J et al., Mol Neurodegen 12:89, 2017).

Example 9: Studies with Compounds of the Invention Showing Activity in Improving Cognitive Function Compounds of the present invention can be investigated for activity in improving cognitive function in a mouse animal model.

Three groups of mice, with at least 13 mice in each group, are given a cognitive acuity test at 7 months. The three groups of mice are: "High Dose" Group (150 mg/kg/day of a compound of the present invention), "Low Dose" (50 mg/kg/day of a compound of the present invention) Group, and a Control Group (not administered a compound of the present invention).

Figure 9:
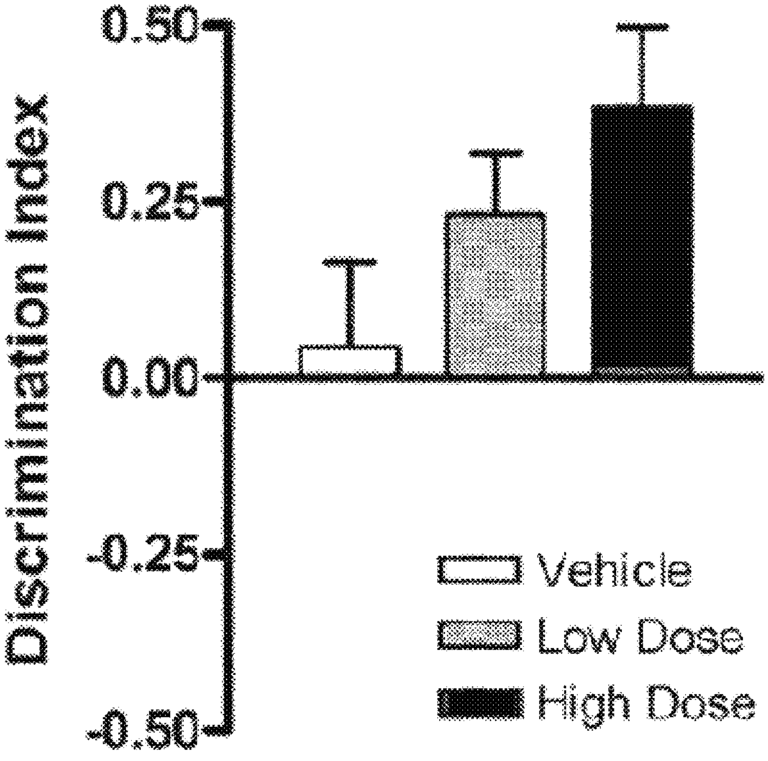
FIG. 9 shows results obtained from mice treated with ambroxol starting at 2 months and tested for novel place recognition at 7 months. This cognitive test measures short-term working memory, involving recognition of a familiar object found in an unfamiliar place (see Magen et al., *Eur J Neurosci* 35:870-882, 2012; Magen and Chesselet, *J Parkinson's Disease* 1:217-227, 2011). A Discrimination Index (DI)=$(t_{novel}-t_{familiar})/(t_{novel}+t_{familiar})$ was used to assess the time spent exploring near the object in a novel place ("$t_{novel}$") vs. the total exploration time overall. Discrimination Index scores greater than zero are considered to indicate good place recognition memory.

The results of such an experiment, but using ambroxol instead of a compound of the present invention, are shown in FIG. 9. A dose-related improvement in cognitive acuity was observed, with the "High Dose" Group showing the best cognitive acuity results, the "Low Dose" Group showing results in between the Control Group and the "High Dose" Group of animals, and the Control Group showing the base line cognitive acuity results. The dosage results are substantially lower than doses previously observed to effectively promote GCase chaperoning activity in mice (e.g., Migdalska-Richards et al., Ann Neurol 80: 766-775, 2016).

Example 10: A Study with Compounds of the Invention Showing Induction of Macroautophagy Compounds of the present invention can be investigated for their ability to induce macroautophagy in mouse cells in culture as follows.

Mouse fibroblasts (NIH3T3) obtained from the American Type Culture Collection (ATCC). Cells are maintained in Dulbecco's modified Eagle's medium (DMEM) (Sigma, St. Louis, MO) in the presence of 10% newborn calf serum (NCS), 50 μg/ml penicillin, and 50 μg/ml streptomycin at 37° C. with 5% CO2. Cells plated in glass-bottom 96-well plates are treated for the indicated time and after fixation, images are acquired using a high-content microscope (Operetta, PerkinElmer). For example, images of 9 different fields per well may be captured, resulting in an average of 2,500-3,000 cells. Nuclei and puncta are identified using the manufacturer's software. The number of particles/puncta per cell can be quantified using the "particle identifier" function in the cytosolic region after thresholding in non-saturated images. In all cases, focal plane thickness is set at 0.17 μm and sections with maximal nucleus diameter selected for quantification. Values may be presented as number of puncta per cell section that in acquisition conditions represents 10-20% of the total puncta per cell. Macroautophagy activity in intact cells is measured upon transduction with lentivirus carrying the mCherry-GFP-LC3 tandem construct (Kimura S et al., Autophagy 3(5):452-460, 2007). Cells plated on glass-bottom 96 well plates and fluorescence are read in both channels. Puncta positive for both fluorophores correspond to autophagosomes, whereas those positive for only the red fluorophore correspond to autolysosomes. Autophagic flux is determined as the conversion of autophagosomes (yellow) to autolysosomes (red only puncta).

FIG. 10 shows the results of an equivalent experiment using ambroxol. It appears that ambroxol may, apart from its pharmacological activity as a GCase chaperone, be inhibiting nutrient sensing. By interfering with nutrient sensing, ambroxol may be triggering a response by the cells of the animal appropriate to the organism entering a nutrient-limited or fasting state, thus sending the organism into a "catabolic signaling" mode characterized by lysosome biogenesis, and autophagy induction, leading to improved lifespan, healthspan and/or cognitive acuity (see, e.g., Efeyan et al., Nature 517:302-310, 2015) (hereby incorporated by reference in its entirety). Thus, ambroxol and analogs of ambroxol and related compounds may systemically inhibit nutrient sensing resulting in the whole organism entering catabolic signaling mode.

The human equivalent doses (HEDs), calculated from the "low" and "high" mouse doses of this study, are approximately 4 mg/kg/day and 12 mg/kg/day, which is approximately 250 mg/day or 750 mg/day for an average 62.5 kg human. Thus, in preferred embodiments, long-term administration of a compound of Formula I (or a pharmaceutically acceptable salt, solvate or prodrug thereof) administered at a dose of approximately 50 mg/day, 75 mg/day, 100 mg/day, 150 mg/day, 200 mg/day 250 mg/day, 300 mg/day, 350 mg/day, 400 mg/day, 450 mg/day, 500 mg/day, 550 mg/day, 600 mg/day, 650 mg/day, 700 mg/day, 750 mg/day, 800 mg/day, 850 mg/day, 900 mg/day, 950 mg/day, 1000 mg/day, 1050 mg/day, 1100 mg/day, 1150 mg/day, 1200 mg/day, or between 50-150 mg/day, 50-200 mg/day, 50-250 mg/day, 250-500 mg/day, 250-1000 mg/day, 1500-2000 mg/day, 1000-1500 mg/day, or 1000-2000 mg/day or less than 1000 mg/day, or approximately 1 mg/kg/day, 2 mg/kg/day, 3 mg/kg/day, 4 mg/kg/day, 5 mg/kg/day, 6 mg/kg/day, 7 mg/kg/day, 8 mg/kg/day, 9 mg/kg/day, 10 mg/kg/day, 11 mg/kg/day, 12 mg/kg/day, and/or between 4-12 mg/kg/day may be expected to be effective in improving healthspan, lifespan, and/or mental acuity.

Example 11: Formulation of Compounds of Formula I into High Drug Loading Liquid Oral Pharmaceutical Compositions and Properties Thereof Preparation of granules—Suitable granules of any one of compounds 1 to 6 (as a representative example of the compounds of the invention) can be prepared as follows: Micronized compound in the form of a powder is placed into a rotor granulator (GXR-35 Rotor Granulator, Freund-Vector Corporation) and a binder solution of hydroxypropylcellulose (HPC-Klucel LF) sprayed onto the powder to form a granular core. Additional compound powder is then co-sprayed with the binder solution to grow the spheres. As layers of compound are added, the particles become more spherical. Resulting spheres may contain 97% by weight of compound of Formula I and 3% by weight of HPC. A particle size (×50) of about 350 microns and a density of about 0.7 g/ml may be achieved.

Application of a water-soluble seal coating to the granules—The compound A granules may be seal coated to generate a smooth and uniform substrate using a bottom-spray fluidized bed coater equipped with a Wurster column. Batch size may be approximately 750 grams. A suitable seal coating contains 9.1% by weight of hypromellose (HPMC); 0.9% by weight of triethyl citrate (TEC); and 90% by weight of water. The granules can be seal coated to a 2% weight gain.

Application of enteric coating to the granules—Seal coated compound granules may be enteric coated using a bottom-spray fluidized bed coater equipped with a Wurster column. Batch size may be approximately 750 grams. A suitable enteric coating contains 58.0% by weight of Eudragit L30D55; 0.9% by weight of triethyl citrate (TEC); 8.7% by weight of Plasacryl T20; and 32.5% by weight of water. The seal coated granules can be enteric coated to a 35% weight gain.

Dissolution Properties—The enteric coated granules can be tested for enteric dissolution properties. The dissolution parameters of equivalent granules comprising ambroxol hydrochloride are shown in Table 4.

TABLE 4

| Dissolution Parameters | |
|---|---|
| Apparatus | II (Paddles) |
| Phase I Media (0-120 minutes) | 750 mL 0.1N HCl |
| Phase II Media (120-240 minutes) | Add 250 mL 0.2M sodium phosphate tribasic to Phase 1. Adjust pH to 6.8 |
| Paddle Speed | 75 rpm |
| Sample Timepoints | 120, 135, 150, 165, 180, 240 minutes |
| Sample Volume | 2 mL |
| Number of Samples | N = 2 |

The disclosures of each and every patent, patent application, and publication cited herein are hereby incorporated herein by reference in their entirety.

While the invention has been disclosed with reference to specific embodiments, it is apparent that other embodiments and variations of this invention may be devised by those skilled in the art without departing from the true spirit and scope of the invention. The appended claims are intended to be construed to include all such embodiments and equivalent variations.

What is claimed is:

1. A compound according to Formula I:

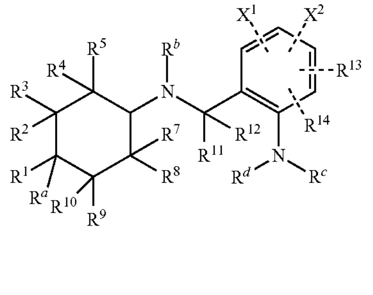

I wherein

...... indicates that the associated R or X group can be attached to any available carbon atom on the phenyl ring, $R^a$ is hydroxyl (OH), $R^b$ is H, $R^c$ and $R^d$ are each independently selected from H or a $C_{1-3}$ alkyl or $R^c$ and $R^d$ are each part of a 4, 5, 6 or 7 membered ring structure that connects $R^c$ and $R^d$, each of $R^1$ to $R^{14}$ is independently selected from H and D, $X^1$ and $X^2$ are independently selected from F, Cl, Br, and I, with the proviso that $X^1$ and $X^2$ are not both Br; or a pharmaceutically acceptable salt, solvate or prodrug thereof.

2. The compound according to claim 1 having the following Formula Ia:

Ia

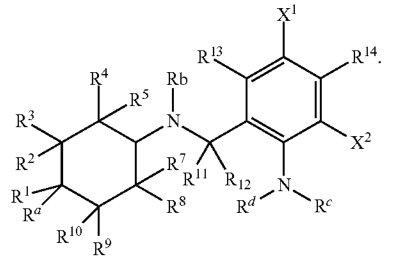

3. The compound according to claim 1 wherein $X^1$ and $X^2$ are both F.

4. The compound according to claim 2 wherein $X^1$ and $X^2$ are both F.

5. The compound according to claim 1 wherein $X^1$ and $X^2$ are both Cl.

6. The compound according to claim 2, wherein $X^1$ and $X^2$ are both Cl.

7. The compound according to claim 1, wherein $X^1$ and $X^2$ are both I.

8. The compound according to claim 1, wherein at least one of $R^1$ to $R^{14}$ is D.

9. The compound according to claim 1, wherein $R^{11}$ or $R^{12}$ is D.

10. The compound of claim 1, as part of a composition comprising a pharmaceutically acceptable carrier.

11. The compound of claim 10, wherein the composition is a liquid oral pharmaceutical composition.

12. The compound of claim 10, wherein the compound of Formula I is in the form of granules having a granular core comprising from about 60 to about 97 weight percent of an active pharmaceutical ingredient and from about 3 to about 40 weight percent of the excipient, wherein the weight percent is based on the total weight of the granular core.

13. The compound of claim 10, wherein the compound of Formula I is in the form of granules having a granular core comprising from about 60 to about 97 weight percent of an active pharmaceutical ingredient and from about 3 to about 40 weight percent of the excipient, wherein the weight percent is based on the total weight of the granular core; wherein the granule core is coated with (iv) a water-soluble seal coating in an amount to provide from about 0.5 to about 5 percent weight gain, and (v) an enteric coating in an amount to provide from about 0.5 to about 50 percent weight gain.

14. A method of preventing and/or treating a disease or medical condition in a subject selected from the group consisting of respiratory diseases and conditions, lysosomal storage disorders (LSDs), and neurological diseases and conditions, said method comprising administering to the subject an effective amount of a compound according to claim 1.

15. The method according to claim 14, wherein the disease or medical condition to be prevented and/or treated is a bronchopulmonary disease, or is Gaucher's disease, Pompe disease or Fabry disease, or is Parkinson's disease, dementia with Lewy bodies, Alzheimer's Disease (AD), Huntington's disease (HD), Amyotrophic Lateral Sclerosis (ALS) (Lou Gehrig's Disease), Frontotemporal Dementia (FTD), Pick's Disease, or Gaucher's Disease.

16. The method according to claim 14, wherein the method is for extending life expectancy of a subject, or for treating, inhibiting or reducing aging of a subject, or for treating, inhibiting or reducing an age-related symptom or an age-related disease in a subject, or for increasing the healthspan, lifespan and/or mental acuity of a subject.

17. The method of claim 14, wherein said method further comprises administration of one or more suitable anti-beta amyloid antibody or fragment thereof.

18. The method of claim 17, wherein the subject is selected by assaying for a biomarker indicative of an at-risk patient or patient in an early stage of development of AD or other amyloid diseases associated with pathological protein misfolding, aggregation and deposition (including Parkinson's disease (PD), Huntington's disease (HD), Amyotrophic Lateral Sclerosis (ALS) (Lou Gehrig's Disease), Pick's Disease, Gaucher's Disease and Frontotemporal degeneration (FTD) disease.

19. The method according to claim 18, wherein the subject is selected by assaying for a phosphorylated tau protein (p-tau) indicative of a patient at-risk of AD or a patient in an early stage of development of AD.

20. The method according to claim 17, wherein the subject is selected by genotyping of at least one gene or locus indicative of a patient at-risk of AD or other diseases associated with pathological protein misfolding, aggregation and deposition (including Parkinson's disease (PD), Huntington's disease (HD), Amyotrophic Lateral Sclerosis (ALS) (Lou Gehrig's Disease), Pick's Disease, Gaucher's Disease and Frontotemporal degeneration (FTD)) disease.

21. The method according to claim 20, wherein the subject is selected by genotyping the ApoE gene or by assaying for p-tau217, p-tau181, p-tau231, p-tau235, and/or N3pG.

22. The method according to claim 21, wherein the subject is selected by genotyping for the ε4 allele of the ApoE gene, or by assaying for p-tau217, p-tau181, p-tau231, p-tau235, and/or N3pG.

23. The method of claim 17, wherein the compound is administered to the subject in a daily dosage selected from a dosage that:

(i) provides a peak concentration in serum of the subject that is greater than 1 μM such as, for example, 2-50 μM, 2-25 μM or 10-20 μM; or (ii) provides a peak concentration in brain tissue of the subject that is greater than 3 μM such as, for example, 5-50 μM, 5-25 μM or 10-20 μM; or (iii) is in the range of about 250-1000 mg/day, 750-1000 mg/day, 1000-2000 mg/day, 1000-1500 mg/day or 1500-2000 mg/day.

24. The compound according to claim 1, wherein $R^1$ is D.

25. The compound of claim 1, wherein the $C_{1-3}$ alkyl is $CH_3$ or $CH_2CH_3$).

26. The compound of claim 1, wherein the membered ring structure is —$R^c$—N—$R^d$—$(CH2)_n$— where n is an integer selected from 1, 2, 3 and 4.

* * * * *